United States Patent
Kaifosh et al.

(10) Patent No.: US 11,179,066 B2
(45) Date of Patent: Nov. 23, 2021

(54) REAL-TIME SPIKE DETECTION AND IDENTIFICATION

(71) Applicant: Facebook Technologies, LLC, Menlo Park, CA (US)

(72) Inventors: Patrick Kaifosh, New York, NY (US); Alexandre Barachant, Brooklyn, NY (US); Michael Isaac Mandel, Brooklyn, NY (US); Daniel Wetmore, Brooklyn, NY (US)

(73) Assignee: Facebook Technologies, LLC, Menlo Park, CA (US)

(*) Notice: Subject to any disclaimer, the term of this patent is extended or adjusted under 35 U.S.C. 154(b) by 8 days.

(21) Appl. No.: 16/539,755

(22) Filed: Aug. 13, 2019

(65) Prior Publication Data
US 2020/0046265 A1    Feb. 13, 2020

Related U.S. Application Data

(60) Provisional application No. 62/718,337, filed on Aug. 13, 2018.

(51) Int. Cl.
*A61B 5/11* (2006.01)
*A61B 5/00* (2006.01)
(Continued)

(52) U.S. Cl.
CPC .......... *A61B 5/1126* (2013.01); *A61B 5/004* (2013.01); *A61B 5/7225* (2013.01);
(Continued)

(58) Field of Classification Search
CPC ... A61B 5/1126; A61B 5/1124; A61B 5/1128; A61B 5/1127; A61B 5/004;
(Continued)

(56) References Cited

U.S. PATENT DOCUMENTS

| 4,055,168 A | 10/1977 | Miller et al. |
| 4,896,120 A | 1/1990 | Kamil |

(Continued)

FOREIGN PATENT DOCUMENTS

| CA | 2902045 A1 | 8/2014 |
| CA | 2921954 A1 | 2/2015 |

(Continued)

OTHER PUBLICATIONS

Wittevrongel, Benjamin et al. "Spatiotemporal Beamforming: A Transparent and Unified Decoding Approach to Synchronous Visual Brain-Computer Interfacing", Frontiers in Neuroscience, vol. 11, Art. 630 (Nov. 15, 2017) (Year: 2017).*

(Continued)

*Primary Examiner* — Matthew Kremer
*Assistant Examiner* — Avery M Foley
(74) *Attorney, Agent, or Firm* — FisherBroyles, LLP

(57) ABSTRACT

Methods and apparatus for substantially real-time detection of spike events in neuromuscular data. The method comprises receiving a plurality of neuromuscular signals from a plurality of neuromuscular sensors arranged on one or more wearable devices worn by a user, detecting, based on the plurality of neuromuscular signals or information derived from the plurality of neuromuscular signals, at least one spike event corresponding to firing of an action potential in at least one motor unit, determining, based on the plurality of neuromuscular signals or the information derived from the plurality of neuromuscular signals, a biological source of the detected at least one spike event, and generating at least one output based, at least in part, on the detected at least one spike event and/or the determined biological source of the detected at least one spike event.

30 Claims, 16 Drawing Sheets

(51) Int. Cl.
  *G06N 3/08* (2006.01)
  *G06N 3/04* (2006.01)
  *G06N 20/20* (2019.01)

(52) U.S. Cl.
  CPC .......... *A61B 5/7267* (2013.01); *A61B 5/7282* (2013.01); *G06N 3/0454* (2013.01); *G06N 3/08* (2013.01); *G06N 20/20* (2019.01); *A61B 2562/0219* (2013.01)

(58) Field of Classification Search
  CPC ... A61B 5/7225; A61B 5/7228; A61B 5/7264; A61B 5/7267; A61B 5/7282; A61B 5/7285; A61B 2562/0219; G06N 20/20; G06N 3/0454; G06N 3/0463; G06N 3/0445; G06N 3/08
  See application file for complete search history.

(56) References Cited

U.S. PATENT DOCUMENTS

| | | | |
|---|---|---|---|
| 5,625,577 | A | 4/1997 | Kunii et al. |
| 6,005,548 | A | 12/1999 | Latypov et al. |
| 6,009,210 | A | 12/1999 | Kang |
| 6,244,873 | B1 | 6/2001 | Hill et al. |
| 6,411,843 | B1 | 6/2002 | Zarychta |
| 6,658,287 | B1 | 12/2003 | Litt et al. |
| 6,720,984 | B1 | 4/2004 | Jorgensen et al. |
| 6,774,885 | B1 | 8/2004 | Even-Zohar |
| 6,942,621 | B2 | 9/2005 | Avinash et al. |
| 7,089,148 | B1 | 8/2006 | Bachmann et al. |
| 7,351,975 | B2 | 4/2008 | Brady et al. |
| 7,574,253 | B2 | 8/2009 | Edney et al. |
| 7,580,742 | B2 | 8/2009 | Tan et al. |
| 7,787,946 | B2 | 8/2010 | Stahmann et al. |
| 7,805,386 | B2 | 9/2010 | Greer |
| 7,901,368 | B2 | 3/2011 | Flaherty et al. |
| 8,170,656 | B2 | 5/2012 | Tan et al. |
| 8,190,249 | B1 | 5/2012 | Gharieb et al. |
| 8,311,623 | B2 | 11/2012 | Sanger |
| 8,351,651 | B2 | 1/2013 | Lee |
| 8,421,634 | B2 | 4/2013 | Tan et al. |
| 8,435,191 | B2 | 5/2013 | Barboutis et al. |
| 8,437,844 | B2 | 5/2013 | Syed Momen et al. |
| 8,447,704 | B2 | 5/2013 | Tan et al. |
| 8,484,022 | B1 | 7/2013 | Vanhoucke |
| 8,718,980 | B2 | 5/2014 | Garudadri et al. |
| 8,744,543 | B2 | 6/2014 | Li et al. |
| 8,754,862 | B2 | 6/2014 | Zaliva |
| D717,685 | S | 11/2014 | Bailey et al. |
| 8,880,163 | B2 | 11/2014 | Barachant et al. |
| 8,890,875 | B2 | 11/2014 | Jammes et al. |
| 8,892,479 | B2 | 11/2014 | Tan et al. |
| 9,037,530 | B2 | 5/2015 | Tan et al. |
| D742,272 | S | 11/2015 | Bailey et al. |
| 9,218,574 | B2 | 12/2015 | Phillipps et al. |
| 9,235,934 | B2 | 1/2016 | Mandella et al. |
| 9,240,069 | B1 | 1/2016 | Li |
| 9,278,453 | B2 | 3/2016 | Assad |
| 9,299,248 | B2 | 3/2016 | Lake et al. |
| D756,359 | S | 5/2016 | Bailey et al. |
| 9,351,653 | B1* | 5/2016 | Harrison ............ A61B 5/04014 |
| 9,367,139 | B2 | 6/2016 | Ataee et al. |
| 9,372,535 | B2 | 6/2016 | Bailey et al. |
| 9,389,694 | B2 | 7/2016 | Ataee et al. |
| 9,408,316 | B2 | 8/2016 | Bailey et al. |
| 9,459,697 | B2 | 10/2016 | Bedikian et al. |
| 9,483,123 | B2 | 11/2016 | Aleem et al. |
| 9,597,015 | B2 | 3/2017 | McNames et al. |
| 9,600,030 | B2 | 3/2017 | Bailey et al. |
| 9,612,661 | B2 | 4/2017 | Wagner et al. |
| 9,613,262 | B2 | 4/2017 | Holz |
| 9,654,477 | B1 | 5/2017 | Kotamraju |
| 9,659,403 | B1 | 5/2017 | Horowitz |
| 9,687,168 | B2 | 6/2017 | John |
| 9,696,795 | B2 | 7/2017 | Marcolina et al. |
| 9,720,515 | B2 | 8/2017 | Wagner et al. |
| 9,741,169 | B1 | 8/2017 | Holz |
| 9,766,709 | B2 | 9/2017 | Holz |
| 9,785,247 | B1 | 10/2017 | Horowitz et al. |
| 9,788,789 | B2 | 10/2017 | Bailey |
| 9,864,431 | B2 | 1/2018 | Keskin et al. |
| 9,867,548 | B2 | 1/2018 | Le et al. |
| 9,880,632 | B2 | 1/2018 | Ataee et al. |
| 9,891,718 | B2 | 2/2018 | Connor |
| 10,042,422 | B2 | 8/2018 | Morun et al. |
| 10,070,799 | B2 | 9/2018 | Ang et al. |
| 10,078,435 | B2 | 9/2018 | Noel |
| 10,101,809 | B2 | 10/2018 | Morun et al. |
| 10,152,082 | B2 | 12/2018 | Bailey |
| 10,188,309 | B2 | 1/2019 | Morun et al. |
| 10,199,008 | B2 | 2/2019 | Aleem et al. |
| 10,203,751 | B2 | 2/2019 | Keskin et al. |
| 10,216,274 | B2 | 2/2019 | Chapeskie et al. |
| 10,251,577 | B2 | 4/2019 | Morun et al. |
| 10,310,601 | B2 | 6/2019 | Morun et al. |
| 10,331,210 | B2 | 6/2019 | Morun et al. |
| 10,362,958 | B2 | 7/2019 | Morun et al. |
| 10,409,371 | B2 | 9/2019 | Kaifosh et al. |
| 10,437,335 | B2 | 10/2019 | Daniels |
| 10,460,455 | B2 | 10/2019 | Giurgica-Tiron et al. |
| 10,489,986 | B2 | 11/2019 | Kaifosh et al. |
| 10,496,168 | B2 | 12/2019 | Kaifosh et al. |
| 10,504,286 | B2 | 12/2019 | Kaifosh et al. |
| 2003/0144829 | A1 | 7/2003 | Geatz et al. |
| 2003/0171921 | A1 | 9/2003 | Manabe et al. |
| 2003/0184544 | A1 | 10/2003 | Prudent |
| 2004/0054273 | A1 | 3/2004 | Finneran et al. |
| 2004/0092839 | A1 | 5/2004 | Shin et al. |
| 2006/0129057 | A1* | 6/2006 | Maekawa ............ A61B 5/0488 600/546 |
| 2007/0009151 | A1 | 1/2007 | Pittman et al. |
| 2007/0172797 | A1 | 7/2007 | Hada et al. |
| 2007/0177770 | A1 | 8/2007 | Derchak et al. |
| 2007/0256494 | A1 | 11/2007 | Nakamura et al. |
| 2007/0285399 | A1 | 12/2007 | Lund |
| 2008/0051673 | A1 | 2/2008 | Kong et al. |
| 2008/0052643 | A1 | 2/2008 | Ike et al. |
| 2008/0103639 | A1 | 5/2008 | Troy et al. |
| 2008/0214360 | A1 | 9/2008 | Stirling et al. |
| 2008/0221487 | A1 | 9/2008 | Zohar et al. |
| 2009/0027337 | A1 | 1/2009 | Hildreth |
| 2009/0079813 | A1 | 3/2009 | Hildreth |
| 2009/0082692 | A1 | 3/2009 | Hale et al. |
| 2009/0082701 | A1 | 3/2009 | Zohar et al. |
| 2009/0112080 | A1 | 4/2009 | Matthews |
| 2009/0124881 | A1 | 5/2009 | Rytky |
| 2009/0326406 | A1 | 12/2009 | Tan et al. |
| 2009/0327171 | A1 | 12/2009 | Tan et al. |
| 2010/0030532 | A1 | 2/2010 | Arora et al. |
| 2010/0063794 | A1 | 3/2010 | Hernandez-Rebollar |
| 2010/0106044 | A1 | 4/2010 | Linderman |
| 2010/0113910 | A1 | 5/2010 | Brauers et al. |
| 2010/0280628 | A1 | 11/2010 | Sankai |
| 2010/0292595 | A1 | 11/2010 | Paul |
| 2010/0292606 | A1* | 11/2010 | Prakash ............ A61B 5/0488 600/554 |
| 2010/0292617 | A1 | 11/2010 | Lei et al. |
| 2010/0293115 | A1 | 11/2010 | Seyed Momen |
| 2010/0315266 | A1 | 12/2010 | Gunawardana et al. |
| 2011/0077484 | A1 | 3/2011 | Van Slyke et al. |
| 2011/0092826 | A1 | 4/2011 | Lee et al. |
| 2011/0173204 | A1 | 7/2011 | Murillo et al. |
| 2011/0173574 | A1 | 7/2011 | Clavin et al. |
| 2011/0230782 | A1 | 9/2011 | Bartol et al. |
| 2012/0066163 | A1 | 3/2012 | Balls et al. |
| 2012/0188158 | A1 | 7/2012 | Tan et al. |
| 2012/0265480 | A1 | 10/2012 | Oshima |
| 2012/0283526 | A1 | 11/2012 | Gommesen et al. |
| 2013/0004033 | A1 | 1/2013 | Trugenberger |
| 2013/0077820 | A1 | 3/2013 | Marais et al. |
| 2013/0123656 | A1 | 5/2013 | Heck |
| 2013/0141375 | A1 | 6/2013 | Ludwig et al. |
| 2013/0207889 | A1 | 8/2013 | Chang et al. |

(56) References Cited

U.S. PATENT DOCUMENTS

| | | |
|---|---|---|
| 2013/0217998 A1 | 8/2013 | Mahfouz et al. |
| 2013/0232095 A1 | 9/2013 | Tan et al. |
| 2013/0317382 A1 | 11/2013 | Le |
| 2013/0317648 A1 | 11/2013 | Assad |
| 2014/0052150 A1 | 2/2014 | Taylor et al. |
| 2014/0092009 A1 | 4/2014 | Yen et al. |
| 2014/0098018 A1 | 4/2014 | Kim et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0223462 A1 | 8/2014 | Aimone et al. |
| 2014/0240103 A1 | 8/2014 | Lake et al. |
| 2014/0240223 A1 | 8/2014 | Lake et al. |
| 2014/0245200 A1 | 8/2014 | Holz |
| 2014/0249397 A1 | 9/2014 | Lake et al. |
| 2014/0277622 A1 | 9/2014 | Raniere |
| 2014/0278441 A1 | 9/2014 | Ton et al. |
| 2014/0297528 A1 | 10/2014 | Agrawal et al. |
| 2014/0304665 A1 | 10/2014 | Holz |
| 2014/0330404 A1 | 11/2014 | Abdelghani et al. |
| 2014/0334083 A1 | 11/2014 | Bailey |
| 2014/0344731 A1 | 11/2014 | Holz |
| 2014/0355825 A1 | 12/2014 | Kim et al. |
| 2014/0358024 A1* | 12/2014 | Nelson ............... A61B 5/04014 600/544 |
| 2014/0361988 A1 | 12/2014 | Katz et al. |
| 2014/0364703 A1 | 12/2014 | Kim et al. |
| 2014/0365163 A1 | 12/2014 | Jallon |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057770 A1 | 2/2015 | Bailey et al. |
| 2015/0070270 A1 | 3/2015 | Bailey et al. |
| 2015/0070274 A1 | 3/2015 | Morozov |
| 2015/0084860 A1 | 3/2015 | Aleem et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0157944 A1 | 6/2015 | Gottlieb |
| 2015/0169074 A1 | 6/2015 | Ataee et al. |
| 2015/0182165 A1 | 7/2015 | Miller et al. |
| 2015/0193949 A1 | 7/2015 | Katz et al. |
| 2015/0223716 A1 | 8/2015 | Korkala et al. |
| 2015/0234426 A1 | 8/2015 | Bailey et al. |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0296553 A1 | 10/2015 | DiFranco et al. |
| 2015/0302168 A1 | 10/2015 | De Sapio et al. |
| 2015/0309563 A1 | 10/2015 | Connor |
| 2015/0309582 A1 | 10/2015 | Gupta |
| 2015/0313496 A1 | 11/2015 | Connor |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0366504 A1 | 12/2015 | Connor |
| 2015/0370326 A1 | 12/2015 | Chapeskie et al. |
| 2015/0370333 A1 | 12/2015 | Ataee et al. |
| 2016/0011668 A1 | 1/2016 | Gilad-Bachrach et al. |
| 2016/0049073 A1 | 2/2016 | Lee |
| 2016/0092504 A1 | 3/2016 | Mitri et al. |
| 2016/0144172 A1 | 5/2016 | Hsueh et al. |
| 2016/0162604 A1 | 6/2016 | Xiaoli et al. |
| 2016/0187992 A1 | 6/2016 | Yamamoto et al. |
| 2016/0235323 A1 | 8/2016 | Tadi et al. |
| 2016/0239080 A1 | 8/2016 | Marcolina et al. |
| 2016/0262687 A1 | 9/2016 | Imperial |
| 2016/0274758 A1 | 9/2016 | Bailey |
| 2016/0275726 A1 | 9/2016 | Mullins |
| 2016/0292497 A1 | 10/2016 | Kehtarnavaz et al. |
| 2016/0313798 A1 | 10/2016 | Connor |
| 2016/0313801 A1 | 10/2016 | Wagner et al. |
| 2016/0313890 A1 | 10/2016 | Walline et al. |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0068445 A1 | 3/2017 | Lee et al. |
| 2017/0080346 A1 | 3/2017 | Abbas |
| 2017/0090604 A1 | 3/2017 | Barbier |
| 2017/0091567 A1 | 3/2017 | Wang et al. |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0161635 A1 | 6/2017 | Oono et al. |
| 2017/0188980 A1 | 7/2017 | Ash |
| 2017/0259167 A1 | 9/2017 | Cook et al. |
| 2017/0285756 A1 | 10/2017 | Wang et al. |
| 2017/0285848 A1 | 10/2017 | Rosenberg et al. |
| 2017/0296363 A1 | 10/2017 | Yetkin et al. |
| 2017/0301630 A1 | 10/2017 | Nguyen et al. |
| 2017/0308118 A1 | 10/2017 | Ito |
| 2017/0344706 A1* | 11/2017 | Torres ............... A61B 5/162 |
| 2017/0347908 A1* | 12/2017 | Watanabe ........... A61B 5/7225 |
| 2018/0000367 A1 | 1/2018 | Longinotti-Buitoni |
| 2018/0020951 A1 | 1/2018 | Kaifosh et al. |
| 2018/0020978 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0064363 A1 | 3/2018 | Morun et al. |
| 2018/0067553 A1 | 3/2018 | Morun et al. |
| 2018/0081439 A1 | 3/2018 | Daniels |
| 2018/0088765 A1 | 3/2018 | Bailey |
| 2018/0092599 A1 | 4/2018 | Kerth et al. |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0120948 A1 | 5/2018 | Aleem et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0178008 A1* | 6/2018 | Bouton ............... A61H 3/00 |
| 2018/0301057 A1 | 10/2018 | Hargrove et al. |
| 2018/0307314 A1 | 10/2018 | Connor |
| 2018/0321745 A1 | 11/2018 | Morun et al. |
| 2018/0321746 A1 | 11/2018 | Morun et al. |
| 2018/0333575 A1 | 11/2018 | Bouton |
| 2018/0344195 A1 | 12/2018 | Morun et al. |
| 2018/0360379 A1 | 12/2018 | Harrison et al. |
| 2019/0008453 A1* | 1/2019 | Spoof ................. A61B 5/4848 |
| 2019/0025919 A1 | 1/2019 | Tadi et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0076716 A1 | 3/2019 | Chiou et al. |
| 2019/0121305 A1 | 4/2019 | Kaifosh et al. |
| 2019/0121306 A1 | 4/2019 | Kaifosh et al. |
| 2019/0146809 A1 | 5/2019 | Lee et al. |
| 2019/0150777 A1 | 5/2019 | Guo et al. |
| 2019/0192037 A1 | 6/2019 | Morun et al. |
| 2019/0212817 A1 | 7/2019 | Kaifosh et al. |
| 2019/0223748 A1 | 7/2019 | Al-natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0247650 A1* | 8/2019 | Tran ................... A61N 1/3625 |
| 2019/0324549 A1 | 10/2019 | Araki et al. |
| 2019/0357787 A1 | 11/2019 | Barachant et al. |
| 2019/0362557 A1 | 11/2019 | Lacey et al. |

(56) References Cited

U.S. PATENT DOCUMENTS

FOREIGN PATENT DOCUMENTS

| | | |
|---|---|---|
| CA | 2939644 A1 | 8/2015 |
| CN | 1838933 A | 9/2006 |
| CN | 103777752 A | 5/2014 |
| CN | 105190578 A | 12/2015 |
| CN | 106102504 A | 11/2016 |
| EP | 2198521 B1 | 6/2012 |
| EP | 2959394 A1 | 12/2015 |
| EP | 3104737 A1 | 12/2016 |
| JP | H05-277080 A | 10/1993 |
| JP | 2005-095561 A | 4/2005 |
| JP | 2010-520561 A | 6/2010 |
| JP | 2016-507851 A | 3/2016 |
| JP | 2017-509386 A | 4/2017 |
| KR | 2015-0123254 A | 11/2015 |
| KR | 2016-0121552 A | 10/2016 |
| KR | 10-1790147 B1 | 10/2017 |
| WO | WO 2008/109248 A2 | 9/2008 |
| WO | WO 2009/042313 A1 | 4/2009 |
| WO | WO 2010/104879 A2 | 9/2010 |
| WO | WO 2012/155157 A1 | 11/2012 |
| WO | WO 2014/130871 A1 | 8/2014 |
| WO | WO 2014/186370 A1 | 11/2014 |
| WO | WO 2014/194257 A1 | 12/2014 |
| WO | WO 2014/197443 A1 | 12/2014 |
| WO | WO 2015/027089 A1 | 2/2015 |
| WO | WO 2015/073713 A1 | 5/2015 |
| WO | WO 2015/081113 A1 | 6/2015 |
| WO | WO 2015/123445 A1 | 8/2015 |
| WO | WO 2015/199747 A1 | 12/2015 |
| WO | WO 2016/041088 A1 | 3/2016 |
| WO | WO 2017/062544 A1 | 4/2017 |
| WO | WO 2017/092225 A1 | 6/2017 |
| WO | WO 2017/120669 A1 | 7/2017 |
| WO | WO 2017/172185 A1 | 10/2017 |
| WO | WO 2017/208167 A1 | 12/2017 |

OTHER PUBLICATIONS

Zacharaki, Evangelia et al. "Spike pattern recognition by supervised classification in low dimensional embedding space", Brain Informatics, Feb. 24, 2016, 3:73-8 (Year: 2016).*
International Preliminary Report on Patentability for International Application No. PCT/US2017/043686 dated Feb. 7, 2019.
International Search Report and Written Opinion for International Application No. PCT/US2017/043686 dated Oct. 6, 2017.
International Preliminary Report on Patentability for International Application No. PCT/US2017/043693 dated Feb. 7, 2019.
International Search Report and Written Opinion for International Application No. PCT/US2017/043693 dated Oct. 6, 2017.
International Preliminary Report on Patentability for International Application No. PCT/US2017/043791 dated Feb. 7, 2019.
International Search Report and Written Opinion for International Application No. PCT/US2017/043791 dated Oct. 5, 2017.
International Preliminary Report on Patentability for International Application No. PCT/US2017/043792 dated Feb. 7, 2019.
International Search Report and Written Opinion for International Application No. PCT/US2017/043792 dated Oct. 5, 2017.
International Search Report and Written Opinion for International Application No. PCT/US2018/056768 dated Jan. 15, 2019.
International Search Report and Written Opinion for International Application No. PCT/US2018/061409 dated Mar. 12, 2019.
International Search Report and Written Opinion for International Application No. PCT/US2018/063215 dated Mar. 21, 2019.
International Search Report and Written Opinion for International Application No. PCT/US2019/015134 dated May 15, 2019.
International Search Report and Written Opinion for International Application No. PCT/US2019/015167 dated May 21, 2019.
International Search Report and Written Opinion for International Application No. PCT/US2019/015174 dated May 21, 2019.
International Search Report and Written Opinion for International Application No. PCT/US2019/015238 dated May 16, 2019.
International Search Report and Written Opinion for International Application No. PCT/US2019/015183 dated May 3, 2019.
International Search Report and Written Opinion for International Application No. PCT/US2019/015180 dated May 28, 2019.
International Search Report and Written Opinion for International Application No. PCT/US2019/015244 dated May 16, 2019.
International Search Report and Written Opinion for International Application No. PCT/US2019/028299 dated Aug. 9, 2019.
International Search Report and Written Opinion for International Application No. PCT/US2019/034173 dated Sep. 18, 2019.
Invitation to Pay Additional Fees for International Application No. PCT/US2019/031114 dated Aug. 6, 2019.
International Search Report and Written Opinion for International Application No. PCT/US19/20065 dated May 16, 2019.
International Search Report and Written Opinion for International Application No. PCT/US2019/037302 dated Oct. 11, 2019.
Invitation to Pay Additional Fees for International Application No. PCT/US2019/049094 dated Oct. 24, 2019.
Arkenbout et al., Robust Hand Motion Tracking through Data Fusion of 5DT Data Glove and Nimble VR Kinect Camera Measurements. Sensors. 2015;15:31644-71.
Benko et al., Enhancing Input on and Above the Interactive Surface with Muscle Sensing. The ACM International Conference on Interactive Tabletops and Surfaces. ITS '09. 2009:93-100.
Boyali et al., Spectral Collaborative Representation based Classification for hand gestures recognition on electromyography signals. Biomedical Signal Processing and Control. 2016;24:11-18.
Cheng et al., A Novel Phonology- and Radical-Coded Chinese Sign Language Recognition Framework Using Accelerometer and Surface Electromyography Sensors. Sensors. 2015;15:23303-24.
Csapo et al., Evaluation of Human-Myo Gesture Control Capabilities in Continuous Search and Select Operations. 7th IEEE International Conference on Cognitive Infocommunications. 2016;000415-20.
Davoodi et al., Development of a Physics-Based Target Shooting Game to Train Amputee Users of Multijoint Upper Limb Prostheses. Presence. Massachusetts Institute of Technology. 2012;21(1):85-95.
Delis et al., Development of a Myoelectric Controller Based on Knee Angle Estimation. Biodevices 2009. International Conference on Biomedical Electronics and Devices. Jan. 17, 2009. 7 pages.
Diener et al., Direct conversion from facial myoelectric signals to speech using Deep Neural Networks. 2015 International Joint Conference on Neural Networks (IJCNN). Oct. 1, 2015. 7 pages.
Ding et al., HMM with improved feature extraction-based feature parameters for identity recognition of gesture command operators by using a sensed Kinect-data stream. Neurocomputing. 2017;262:108-19.
Farina et al., Man/machine interface based on the discharge timings of spinal motor neurons after targeted muscle reinnervation. Nature. Biomedical Engineering. 2017;1:1-12.
Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.
Gallina et al., Surface EMG Biofeedback. Surface Electromyography: Physiology, Engineering, and Applications. 2016:485-500.
Gopura et al., A Human Forearm and wrist motion assist exoskeleton robot with EMG-based fuzzy-neuro control. Proceedings of the 2nd IEEE/RAS-EMBS International Conference on Biomedical Robotics and Biomechatronics. Oct. 19-22, 2008. 6 pages.
Hauschild et al., A Virtual Reality Environment for Designing and Fitting Neural Prosthetic Limbs. IEEE Transactions on Neural Systems and Rehabilitation Engineering. 2007;15(1):9-15.
Jiang, Purdue University Graduate School Thesis/Dissertation Acceptance. Graduate School Form 30. Updated Jan. 15, 2015. 24 pages.
Kawaguchi et al., Estimation of Finger Joint Angles Based on Electromechanical Sensing of Wrist Shape. IEEE Transactions on Neural Systems and Rehabilitation Engineering. 2017;25(9):1409-18.

(56) References Cited

OTHER PUBLICATIONS

Kim et al., Real-Time Human Pose Estimation and Gesture Recognition from Depth Images Using Superpixels and SVM Classifier. Sensors. 2015;15:12410-27.
Koerner, Design and Characterization of the Exo-Skin Haptic Device: A Novel Tendon Actuated Textile Hand Exoskeleton. 2017. 5 pages.
Lee et al., Motion and Force Estimation System of Human Fingers. Journal of Institute of Control, Robotics and Systems. 2011;17(10):1014-1020.
Li et al., Motor Function Evaluation of Hemiplegic Upper-Extremities Using Data Fusion from Wearable Inertial and Surface EMG Sensors. Sensors. MDPI. 2017;17(582):1-17.
Lopes et al., Hand/arm gesture segmentation by motion using IMU and EMG sensing. ScienceDirect. Elsevier. Procedia Manufacturing. 2017;11:107-13.
Martin et al., A Novel Approach of Prosthetic Arm Control using Computer Vision, Biosignals, and Motion Capture. IEEE. 2014. 5 pages.
McIntee, A Task Model of Free-Space Movement-Based Gestures. Dissertation. Graduate Faculty of North Carolina State University. Computer Science. 2016. 129 pages.
Mendes et al., Sensor Fusion and Smart Sensor in Sports and Biomedical Applications. Sensors. 2016;16(1569):1-31.
Mohamed, Homogeneous cognitive based biometrics for static authentication. Dissertation submitted to University of Victoria, Canada. 2010. 149 pages. URL:http://hdl.handle.net/1828/3211 [last accessed Oct. 11, 2019].
Naik et al., Source Separation and Identification issues in bio signals: A solution using Blind source separation. Intech. 2009. 23 pages.
Naik et al., Subtle Hand gesture identification for HCI using Temporal Decorrelation Source Separation BSS of surface EMG. Digital Image Computing Techniques and Applications. IEEE Computer Society. 2007;30-7.
Negro et al., Multi-channel intramuscular and surface EMG decomposition by convolutive blind source separation. Journal of Neural Engineering. 2016;13:1-17.
Saponas et al., Demonstrating the Feasibility of Using Forearm Electromyography for Muscle-Computer Interfaces. CHI 2008 Proceedings. Physiological Sensing for Input. 2008:515-24.
Saponas et al., Enabling Always-Available Input with Muscle-Computer Interfaces. UIST '09. 2009:167-76.
Saponas et al., Making Muscle-Computer Interfaces More Practical. CHI 2010: Brauns and Brawn. 2010:851-4.
Sartori et al., Neural Data-Driven Musculoskeletal Modeling for Personalized Neurorehabilitation Technologies. IEEE Transactions on Biomedical Engineering. 2016;63(5):879-93.
Sauras-Perez et al., A Voice and Pointing Gesture Interaction System for Supporting Human Spontaneous Decisions in Autonomous Cars. Clemson University. All Dissertations. 2017. 174 pages.
Shen et al., I am a Smartwatch and I can Track my User's Arm. University of Illinois at Urbana-Champaign. MobiSys' 16. 12 pages.
Son et al., Evaluating the utility of two gestural discomfort evaluation methods. PLOS One. 2017. 21 pages.
Strbac et al., Microsoft Kinect-Based Artificial Perception System for Control of Functional Electrical Stimulation Assisted Grasping. Hindawi Publishing Corporation. BioMed Research International. 2014. 13 pages.
Torres, Myo Gesture Control Armband. PCMag. Https://www.pcmag.com/article2/0,2817,2485462,00.asp 2015. 9 pages.
Valero-Cuevas et al., Computational Models for Neuromuscular Function. NIH Public Access Author Manuscript. Jun. 16, 2011. 52 pages.
Wodzinski et al., Sequential Classification of Palm Gestures Based on A* Algorithm and MLP Neural Network for Quadrocopter Control. Metrol. Meas. Syst., 2017;24(2):265-76.
Xue et al., Multiple Sensors Based Hand Motion Recognition Using Adaptive Directed Acyclic Graph. Applied Sciences. MDPI. 2017;7(358):1-14.
Yang et al., Surface EMG based handgrip force predictions using gene expression programming. Neurocomputing. 2016;207:568-579.
Extended European Search Report for European Application No. EP 17835111.0 dated Nov. 21, 2019.
Extended European Search Report for European Application No. EP 17835140.9 dated Nov. 26, 2019.
International Search Report and Written Opinion for International Application No. PCT/US2019/042579 dated Oct. 31, 2019.
International Search Report and Written Opinion for International Application No. PCT/US2019/052131 dated Dec. 6, 2019.
International Search Report and Written Opinion for International Application No. PCT/US2019/046351 dated Nov. 7, 2019.
Al-Mashhadany, Inverse Kinematics Problem (IKP) of 6-DOF Manipulator Bgy Locally Recurrent Neural Networks (LRNNs). Management and Service Science (MASS). 2010 International Conference ON, IEEE. Aug. 24, 2010. 5 pages. ISBN: 978-1-4244-5325-2.
Kipke et al., Silicon-substrate Intracortical Microelectrode Arrays for Long-Term Recording of Neuronal Spike Activity in Cerebral Cortex. IEEE Transactions on Neural Systems and Rehabilitation Engineering. 2003;11(2):151-155.
Marcard et al., Sparse Inertial Poser: Automatic 3D Human Pose Estimation from Sparse IMUs. Eurographics. 2017;36(2). 12 pages.

\* cited by examiner

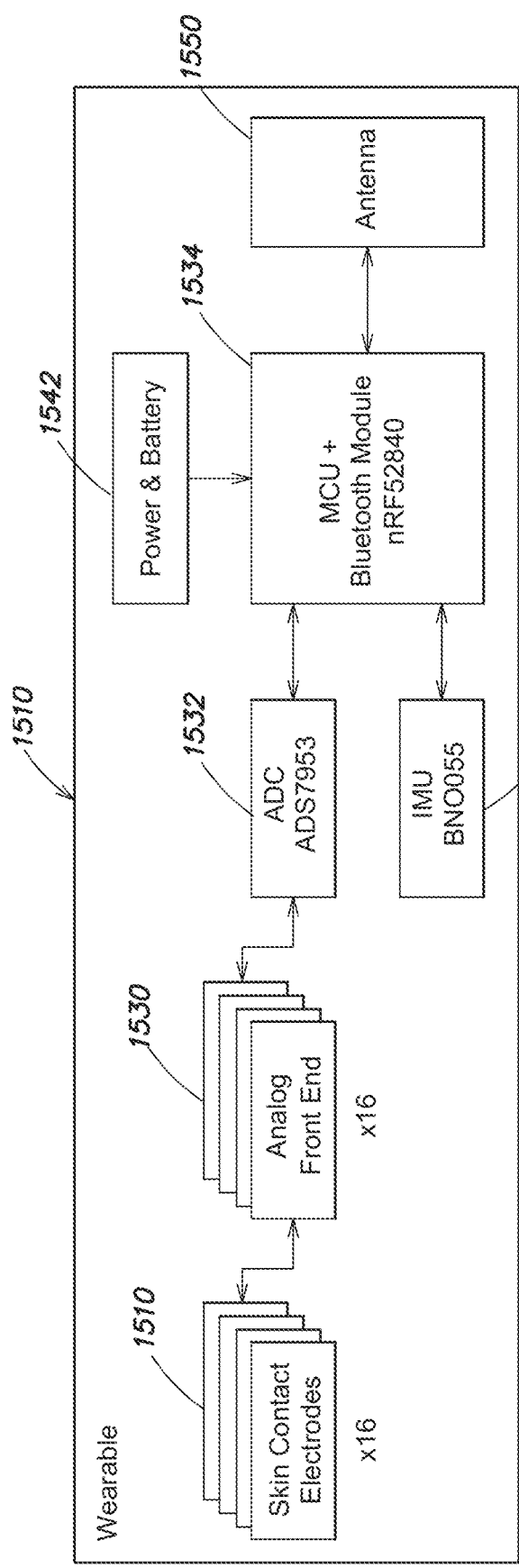
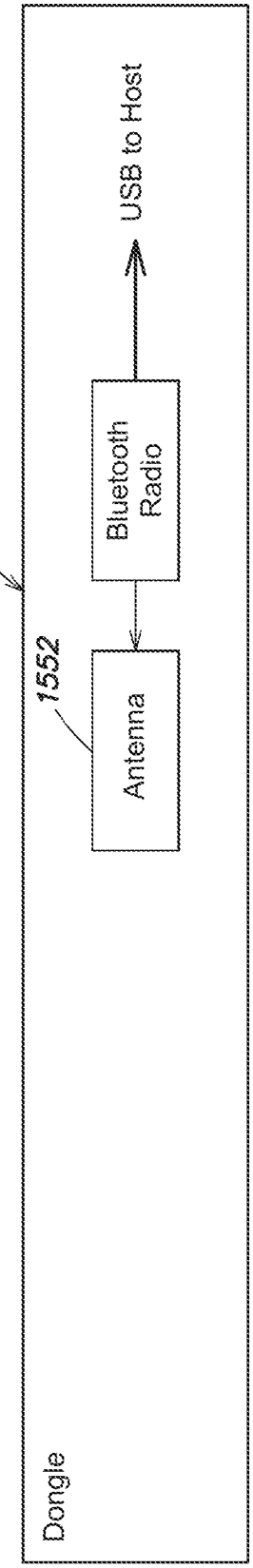
FIG. 15A
FIG. 15B

REAL-TIME SPIKE DETECTION AND IDENTIFICATION

RELATED APPLICATIONS

This application is a Non-Provisional of Provisional (35 USC § 119(e)) of U.S. Application Ser. No. 62/718,337, filed Aug. 13, 2018, entitled "REAL-TIME SPIKE DETECTION AND IDENTIFICATION", which is incorporated by reference in its entirety.

BACKGROUND

Neuromuscular signals arising from the human central nervous system may reflect neural activation that results in the contraction of one or more muscles in the human body. Neuromuscular sensors, an example of which includes electromyography (EMG) sensors, placed on the surface of the human body record neuromuscular activity produced when skeletal muscle cells are activated. The neuromuscular activity measured by neuromuscular sensors may result from neural activation, muscle excitation, muscle contraction, or a combination of the neural activation and muscle contraction. Signals recorded by neuromuscular sensors are routinely used to assess neuromuscular dysfunction in patients with motor control disorders and have been used in some applications as control signals for devices such as prosthetic limbs.

SUMMARY

Coordinated movements of skeletal muscles in the human body that collectively result in the performance of a motor task originate with neural signals arising in the central nervous system. The neural signals travel from the central nervous system to muscles via spinal motor neurons, each of which has a cell body in the spinal cord and axon terminals on one or more muscle fibers. In response to receiving the neural signals, the muscle fibers contract resulting in muscle movement. A spinal motor neuron and the muscle fiber(s) it innervates are collectively referred to as a "motor unit." Muscles typically include muscle fibers from hundreds of motor units and simultaneous contraction of muscle fibers in multiple motor units is usually required for muscle contraction that results in movement of a skeletal segment and/or a force to be exerted by a part of the body.

Muscles exhibit a characteristic pattern of motor unit recruitment in which motor units are activated in sequence, where the number of motor units activated depends on a strength of a desired muscle contraction. When a motor unit is activated, a motor unit action potential (MUAP) is generated in each of the muscle fibers of the motor unit. Neuromuscular sensors such as electromyography (EMG) sensors record electrochemical signals that result in motor activity, such as contraction of a muscle. In the case of EMG sensors arranged on the surface of the human body, the biological signals recorded relate to the generation of MUAPs in muscle fibers of a motor unit. A MUAP only occurs when the corresponding motor unit is triggered by its motor neuron. Some embodiments are directed to analyzing neuromuscular signals to identify spike events in a motor neuron of a motor unit that results in the generation of MUAPs in the muscle fibers of the motor unit. Control signals determined based on one or more identified spike events may be used in some embodiments to control the operation of a device.

Some embodiments are directed to a computerized system. The computerized system comprises a plurality of neuromuscular sensors configured to record a plurality of neuromuscular signals from a user, wherein the plurality of neuromuscular sensors are arranged on one or more wearable devices, and at least one computer processor. The at least one computer processor is programmed to detect, based on the plurality of neuromuscular signals or information derived from the plurality of neuromuscular signals, at least one spike event corresponding to firing of an action potential in at least one motor unit, determine, based on the plurality of neuromuscular signals or the information derived from the plurality of neuromuscular signals, a biological source of the detected at least one spike event, and generate at least one output based, at least in part, on the detected at least one spike event and/or the determined biological source of the detected at least one spike event.

According to one aspect, a computerized system is provided. The system comprises a plurality of neuromuscular sensors configured to record a plurality of neuromuscular signals from a user, wherein the plurality of neuromuscular sensors are arranged on one or more wearable devices, at least one computer processor programmed to detect, based on the plurality of neuromuscular signals or information derived from the plurality of neuromuscular signals, at least one spike event corresponding to firing of an action potential in at least one motor unit, determine, based on the plurality of neuromuscular signals or the information derived from the plurality of neuromuscular signals, a biological source of the detected at least one spike event, and generate at least one output based, at least in part, on the detected at least one spike event and/or the determined biological source of the detected at least one spike event.

According to one embodiment, at least one computer processor is further programmed to apply one or more criteria for selecting a best biological source from a plurality of biological sources associated with respective detected spike events, select at least one best spike event associated with the best biological source, and subtract a detected waveform for the at least best spike event from at least one of the neuromuscular signals, and generating a residual neuromuscular signal. According to one embodiment, at least one computer processor is further programmed to perform an iterative process for processing detected spike events until no biological source is present within the residual signal that meets a minimum threshold for selection as a biological source for spike events. According to one embodiment, the at least one computer processor is further programmed to group detected spike events into a muscle-specific group based on co-activations and sort spike events within the muscle-specific group to approximate a recruitment curve. According to one embodiment, at least one computer processor is further programmed to apply at least one filter to a time-lagged representation of the plurality of neuromuscular signals, and wherein detecting the at least one spike event and determining the biological source of the detected at least one spike event is performed based on the filtered time-lagged representation of the plurality of neuromuscular signals.

According to one embodiment, applying at least one filter to a time-lagged representation of the plurality of neuromuscular sensors comprises using a beamforming process to apply a plurality of beamforming filters to the time-lagged representation of the plurality of neuromuscular signals, wherein the plurality of beamforming filters are filters generated based on spatiotemporal patterns of one or more spike events. According to one embodiment, the beamforming process comprises using a minimum variance distortionless response technique. According to one embodiment, the beamforming process comprises using a linear constrained minimum variance technique.

According to one embodiment, the at least one computer processor is further programmed to determine the spatiotemporal patterns of the one or more spike events corresponding to the plurality of beamforming filters. According to one embodiment, determining the spatiotemporal patterns of the one or more spike events corresponding to the plurality of beamforming filters comprises detecting a plurality of spike events in recorded neuromuscular signals, clustering the detected plurality of spike events, and determining the spatiotemporal patterns based on the clusters of spike events. According to one embodiment, detecting a plurality of spike events comprises detecting within the plurality of neuromuscular signals, periods of low activity, and detecting within the period of low activity, putative spike events. According to one embodiment, detecting the plurality of spike events further comprises analyzing the detected putative spike events to discard spike events having one or more particular characteristics. According to one embodiment, the one or more particular characteristics include a duration longer than a particular threshold duration.

According to one embodiment, the at least one computer processor is further programmed to detect the at least one spike event and/or determine the biological source of the detected at least one spike event using one or more neural networks. According to one embodiment, the one or more neural networks includes a convolutional neural network. According to one embodiment, the one or more neural networks includes a recurrent neural network. According to one embodiment, the at least one computer processor is further programmed to detect the at least one spike event and determine the biological source of the detected at least one spike event using a multi-step iterative technique to decompose a time-lagged representation of the plurality of neuromuscular signals into signal components corresponding to at least one biological source, and detecting the at least one spike event from the at least one biological source. According to one embodiment, the multi-step iterative technique comprises matrix factorization.

According to one embodiment, generating at least one output comprises generating compressed data including an indication of the at least one spike event. According to one embodiment, the indication of the at least one spike event is provided as a control signal to a computer-based system. According to one embodiment, the indication of the at least one spike event is provided as at least one of a group comprising a discrete control signal, a continuous control signal, and a composite control signal. According to one embodiment, generating at least one output comprises generating an indication of the at least one spike event. According to one embodiment, the indication of the at least one spike event includes an indication of a biological source of the at least one spike event and a time of occurrence of the at least one spike event.

According to one embodiment, the at least one computer processor is programmed to provide feedback to the user responsive to the at least one output based, at least in part, on the detected at least one spike event and/or the determined biological source of the detected at least one spike event. According to one embodiment, the at least one computer processor is programmed to provide feedback to the user as part of a user training process. According to one embodiment, the feedback includes at least one of a group comprising auditory, visual, haptic, and multi-sensory feedback. According to one embodiment, the system further comprises an inertial sensor configured to determine movement artifacts or shifts in spatial location of muscle fibers of the at least one motor unit relative to one or more of the plurality of neuromuscular sensors. According to one embodiment, the at least one computer processor is programmed to filter or refine an output of an inferential model responsive to an output of the inertial sensor.

According to one embodiment, the at least one computer processor is further programmed to transmit the compressed data including an indication of the at least one spike event over one or more wireless networks to an external device. According to one embodiment, the system further comprises at least one storage device, and at least one computer processor is further programmed to store the compressed data on the at least one storage device.

According to one embodiment, generating at least one output comprises generating an updated computerized musculoskeletal representation comprising a plurality of rigid body segments connected by joints, wherein generating the updated computerized musculoskeletal representation comprises determining based, at least in part, on the detected at least one spike event and/or the identified biological source of the detected at least one spike event, musculoskeletal position information describing a spatial relationship between two or more connected segments of the plurality of rigid body segments of the computerized musculoskeletal representation and/or force information describing a force between two or more segments of the plurality of rigid body segments of the computerized musculoskeletal representation, and updating the computerized musculoskeletal representation based, at least in part, on the musculoskeletal position information and/or the force information. According to one embodiment, determining the musculoskeletal position information and/or the force information comprises providing as input to a trained inferential model, the detected at least one spike event and/or the identified biological source of the detected at least one spike event, and the musculoskeletal position information and/or the force information is determined based, at least in part, on an output of the trained inferential model.

According to one embodiment, generating at least one output comprises generating in substantially real-time, at least one control signal for controlling at least one device. According to one embodiment, detecting at least one spike event comprises detecting a spatiotemporal pattern of the at least one spike event, and generating at least one control signal comprises generating the at least one control signal based, at least in part, on at least one characteristic of the detected spatiotemporal pattern of the at least one spike event. According to one embodiment, the at least one characteristic comprises a rate of the at least one spike event and/or a spatial distribution of the detected spatiotemporal pattern of the at least one spike event. According to one embodiment, the identified biological source comprises a motor unit. According to one embodiment, the identified biological source comprises a plurality of motor units. According to one embodiment, the identified biological source comprises a muscle. According to one embodiment, the identified biological source comprises a plurality of muscles.

According to one embodiment, determining the biological source of the at least one spike event comprises determining that the at least one spike event is associated with a motor unit or group of motor units, at least one computer processor is further programmed to determine a muscle to which the motor unit or group of motor units belongs, and wherein generating at least one output comprises generating the at least one output based on the determined muscle to which the motor unit or group of motor units belongs. According to one embodiment, the determined muscle is associated with a motor unit recruitment sequence describing a sequence of activation of motor units for the determined muscle, and wherein the at least one computer processor is further programmed to determine where the motor unit or group of motor units fall within the motor unit recruitment sequence of the determined muscle.

According to one embodiment, the system further comprises at least one auxiliary sensor configured to record a plurality of auxiliary signals, and wherein the at least one computer processor is further programmed to generate the at least one output based, at least in part, on the plurality of auxiliary signals. According to one embodiment, the at least one auxiliary sensor comprises at least one inertial measurement unit (IMU) sensor configured to record a plurality of IMU signals, and wherein the at least one computer processor is further programmed to generate the at least one output based, at least in part, on the plurality of IMU signals and/or information derived from the plurality of IMU signals. According to one embodiment, at least one auxiliary sensor comprises at least one camera configured to record one or more images, and wherein the at least one computer processor is further programmed to generate the at least one output based, at least in part, on the one or more images and/or information derived from the one or more images. According to one embodiment, detecting the at least one spike event is further based on the one or more images and/or the information derived from the one or more images.

According to one embodiment, the at least one computer processor is included as a portion of a device separate from and in communication with the plurality of neuromuscular sensors arranged on the one or more wearable devices, and wherein the plurality of neuromuscular sensors are configured to wireless stream in substantially real-time, the plurality of neuromuscular signals and/or the information derived from the plurality of neuromuscular signals to the at least one computer processor. According to one embodiment, the device separate from and in communication with the plurality of neuromuscular sensors is a device selected from the group consisting of a remote server, a desktop computer, a laptop computer, a smartphone, and a wearable electronic device. According to one embodiment, the wearable electronic device is a smartwatch, a health monitoring device, smart glasses, or an augmented reality system. According to one embodiment, at least one computer processor is integrated with the one or more wearable devices on which the plurality of neuromuscular sensors are arranged.

According to one embodiment, at least one computer processor comprises at least one first computer processor included as a portion of a device separate from and in communication with the plurality of neuromuscular sensors arranged on the one or more wearable devices and at least one second computer processor integrated with the one or more wearable devices on which the plurality of neuromuscular sensors are arranged. According to one embodiment, the plurality of neuromuscular sensors are configured to transmit at least some of the plurality of neuromuscular signals to the at least one first computer processor, wherein the at least one first computer processor is programmed to train, based on the at least some of the plurality of neuromuscular signals transmitted from the plurality of neuromuscular sensors, at least one spike detection model and/or at least one spike identification model, transmit the trained at least one spike detection model and/or the at least one spike identification model to the at least one second computer processor, and wherein the at least one second computer processor is programmed to detect the at least one spike event and determine the biological source of the detected at least one spike event using the at least one spike detection model and/or the at least one spike identification model transmitted from the at least one first computer processor.

According to one embodiment, the at least one spike detection model and/or at least one spike identification model are trained to estimate at least one of a group comprising whether the user is activating a particular motor unit, whether the user is activating a particular motor unit with a particular timing, and whether the user is activating a particular combination of motor units. According to one embodiment, detecting at least one spike event corresponding to firing of an action potential in at least one motor unit comprises detecting at least one spike event corresponding to firing of an action potential in a plurality of motor units. According to one embodiment, at least one computer processor is further programmed to threshold the filtered time-lagged representation of the plurality of neuromuscular signals to detect the at least one spike event.

According to one aspect, a computer-implemented method of detecting spike events in neuromuscular data is provided. The method comprises receiving a plurality of neuromuscular signals from a plurality of neuromuscular sensors arranged on one or more wearable devices worn by a user, detecting, based on the plurality of neuromuscular signals or information derived from the plurality of neuromuscular signals, at least one spike event corresponding to firing of an action potential in at least one motor unit, determining, based on the plurality of neuromuscular signals or the information derived from the plurality of neuromuscular signals, a biological source of the detected at least one spike event, and generating at least one output based, at least in part, on the detected at least one spike event and/or the determined biological source of the detected at least one spike event.

According to one embodiment the method further comprises applying one or more criteria for selecting a best biological source from a plurality of biological sources associated with respective detected spike events, selecting at least one best spike event associated with the best biological source, and subtracting a detected waveform for the at least best spike event from at least one of the neuromuscular signals, and generating a residual neuromuscular signal. According to one embodiment, the method further comprises performing an iterative process for processing detected spike events until no biological source is present within the residual signal that meets a minimum threshold for selection as a biological source for spike events. According to one embodiment, the method further comprises grouping detected spike events into a muscle-specific group based on co-activations and sorting spike events within the muscle-specific group to approximate a recruitment curve.

According to one embodiment, the method further comprises applying at least one filter to a time-lagged representation of the plurality of neuromuscular signals, and wherein detecting the at least one spike event and determining the biological source of the detected at least one spike event is performed based on the filtered time-lagged representation of the plurality of neuromuscular signals. According to one embodiment, applying at least one filter to a time-lagged representation of the plurality of neuromuscular sensors comprises using a beamforming process to apply a plurality of beamforming filters to the time-lagged representation of the plurality of neuromuscular signals, wherein the plurality of beamforming filters are filters generated based on spatiotemporal patterns of one or more spike events. According to one embodiment, the beamforming process comprises using a minimum variance distortionless response technique. According to one embodiment, the beamforming process comprises using a linear constrained minimum variance technique.

According to one embodiment, the method further comprises determining the spatiotemporal patterns of the one or more spike events corresponding to the plurality of beamforming filters. According to one embodiment, determining the spatiotemporal patterns of the one or more spike events corresponding to the plurality of beamforming filters comprises detecting a plurality of spike events in recorded neuromuscular signals, clustering the detected plurality of spike events, and determining the spatiotemporal patterns based on the clusters of spike events. According to one embodiment, detecting a plurality of spike events comprises detecting within the plurality of neuromuscular signals, periods of low activity; and detecting within the period of low activity, putative spike events. According to one embodiment, detecting the plurality of spike events further comprises analyzing the detected putative spike events to discard spike events having one or more particular characteristics. According to one embodiment, the one or more particular characteristics include a duration longer than a particular threshold duration.

According to one embodiment, method further comprises detecting the at least one spike event and/or determine the biological source of the detected at least one spike event using one or more neural networks. According to one embodiment, the one or more neural networks includes a convolutional neural network. According to one embodiment, the one or more neural networks includes a recurrent neural network. According to one embodiment, the method further comprises detecting the at least one spike event and determining the biological source of the detected at least one spike event using a multi-step iterative technique to decompose a time-lagged representation of the plurality of neuromuscular signals into signal components corresponding to at least one biological source, and detecting the at least one spike event from the at least one biological source. According to one embodiment, the multi-step iterative technique comprises matrix factorization.

According to one embodiment, generating at least one output comprises generating compressed data including an indication of the at least one spike event. According to one embodiment, the indication of the at least one spike event is provided as a control signal to a computer-based system. According to one embodiment, the indication of the at least one spike event is provided as at least one of a group comprising a discrete control signal, a continuous control signal, and a composite control signal. According to one embodiment, generating at least one output comprises generating an indication of the at least one spike event. According to one embodiment, the indication of the at least one spike event includes an indication of a biological source of the at least one spike event and a time of occurrence of the at least one spike event.

According to one embodiment, the method further comprises providing feedback to the user responsive to the at least one output based, at least in part, on the detected at least one spike event and/or the determined biological source of the detected at least one spike event. According to one embodiment, the method further comprises providing feedback to the user as part of a user training process. According to one embodiment, the feedback includes at least one of a group comprising auditory, visual, haptic, and multi-sensory feedback. According to one embodiment, the wearable device further comprises an inertial sensor, and wherein the method further comprises determining, using the inertial sensor, movement artifacts or shifts in spatial location of muscle fibers of the at least one motor unit relative to one or more of the plurality of neuromuscular sensors. According to one embodiment, the method further comprising filtering or refining an output of an inferential model responsive to an output of the inertial sensor.

According to one embodiment, the method further comprises transmitting the compressed data including an indication of the at least one spike event over one or more wireless networks to an external device. According to one embodiment, at least one of the one or more wearable devices includes at least one storage device, and wherein the method further comprises storing the compressed data on the at least one storage device.

According to one embodiment, generating at least one output comprises generating an updated computerized musculoskeletal representation comprising a plurality of rigid body segments connected by joints, wherein generating the updated computerized musculoskeletal representation comprises determining based, at least in part, on the detected at least one spike event and/or the identified biological source of the detected at least one spike event, musculoskeletal position information describing a spatial relationship between two or more connected segments of the plurality of rigid body segments of the computerized musculoskeletal representation and/or force information describing a force between two or more segments of the plurality of rigid body segments of the computerized musculoskeletal representation, and updating the computerized musculoskeletal representation based, at least in part, on the musculoskeletal position information and/or the force information. According to one embodiment, determining the musculoskeletal position information and/or the force information comprises providing as input to a trained inferential model, the detected at least one spike event and/or the identified biological source of the detected at least one spike event, and wherein the musculoskeletal position information and/or the force information is determined based, at least in part, on an output of the trained inferential model.

According to one embodiment, generating at least one output comprises generating in substantially real-time, at least one control signal for controlling at least one device. According to one embodiment, detecting at least one spike event comprises detecting a spatiotemporal pattern of the at least one spike event, and wherein generating at least one control signal comprises generating the at least one control signal based, at least in part, on at least one characteristic of the detected spatiotemporal pattern of the at least one spike event. According to one embodiment, at least one characteristic comprises a rate of the at least one spike event and/or a spatial distribution of the detected spatiotemporal pattern of the at least one spike event. According to one embodiment, the identified biological source comprises a motor unit. According to one embodiment, the identified biological source comprises a plurality of motor units. According to one embodiment, the identified biological source comprises a muscle. According to one embodiment, the identified biological source comprises a plurality of muscles.

According to one embodiment, determining the biological source of the at least one spike event comprises determining that the at least one spike event is associated with a motor unit or group of motor units, wherein the method further comprises determining a muscle to which the motor unit or group of motor units belongs, and wherein generating at least one output comprises generating the at least one output based on the determined muscle to which the motor unit or group of motor units belongs. According to one embodiment, the determined muscle is associated with a motor unit recruitment sequence describing a sequence of activation of motor units for the determined muscle, and wherein the method further comprises determining where the motor unit or group of motor units fall within the motor unit recruitment sequence of the determined muscle.

According to one embodiment, at least one of the one or more wearable devices includes at least one auxiliary sensor configured to record a plurality of auxiliary signals, and wherein the method further comprises generating the at least one output based, at least in part, on the plurality of auxiliary signals. According to one embodiment, the at least one auxiliary sensor comprises at least one inertial measurement unit (IMU) sensor configured to record a plurality of IMU signals, and wherein the method further comprises generating the at least one output based, at least in part, on the plurality of IMU signals and/or information derived from the plurality of IMU signals. According to one embodiment, the at least one auxiliary sensor comprises at least one camera configured to record one or more images, and wherein the method further comprises generating the at least one output based, at least in part, on the one or more images and/or information derived from the one or more images. According to one embodiment, detecting the at least one spike event is further based on the one or more images and/or the information derived from the one or more images.

According to one embodiment, at least one computer processor is included as a portion of a device separate from and in communication with the plurality of neuromuscular sensors arranged on the one or more wearable devices, and wherein the method further comprises streaming, from the plurality of neuromuscular sensors in substantially real-time, the plurality of neuromuscular signals and/or the information derived from the plurality of neuromuscular signals to the at least one computer processor. According to one embodiment, the device separate from and in communication with the plurality of neuromuscular sensors is a device selected from the group consisting of a remote server, a desktop computer, a laptop computer, a smartphone, and a wearable electronic device. According to one embodiment, the wearable electronic device is a smartwatch, a health monitoring device, smart glasses, or an augmented reality system. According to one embodiment, the method further comprises integrating at least one computer processor with the one or more wearable devices on which the plurality of neuromuscular sensors are arranged.

According to one embodiment, at least one computer processor comprises at least one first computer processor included as a portion of a device separate from and in communication with the plurality of neuromuscular sensors arranged on the one or more wearable devices and at least one second computer processor integrated with the one or more wearable devices on which the plurality of neuromuscular sensors are arranged. According to one embodiment, the method further comprises transmitting, by the plurality of neuromuscular sensors, at least some of the plurality of neuromuscular signals to the at least one first computer processor, and wherein the at least one first computer processor performs acts of training, based on the at least some of the plurality of neuromuscular signals transmitted from the plurality of neuromuscular sensors, at least one spike detection model and/or at least one spike identification model, and transmitting the trained at least one spike detection model and/or the at least one spike identification model to the at least one second computer processor, and wherein the at least one second computer processor performs an act of detecting the at least one spike event and determine the biological source of the detected at least one spike event using the at least one spike detection model and/or the at least one spike identification model transmitted from the at least one first computer processor.

According to one embodiment, the method further comprises training the at least one spike detection model and/or at least one spike identification model to estimate at least one of a group comprising whether the user is activating a particular motor unit, whether the user is activating a particular motor unit with a particular timing, and whether the user is activating a particular combination of motor units. According to one embodiment, detecting at least one spike event corresponding to firing of an action potential in at least one motor unit comprises detecting at least one spike event corresponding to firing of an action potential in a plurality of motor units. According to one embodiment, the method further comprises thresholding the filtered time-lagged representation of the plurality of neuromuscular signals to detect the at least one spike event.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures, several of which are provided in color as indicated. It should be appreciated that the figures are not necessarily drawn to scale.

FIGS. 15A and 15B schematically illustrate components of a computer-based system on which some embodiments are implemented. FIG. 15A illustrates a wearable portion of the computer-based system and FIG. 15B illustrates a dongle portion connected to a computer, wherein the dongle portion is configured to communicate with the wearable portion.

DETAILED DESCRIPTION

Figure 1:
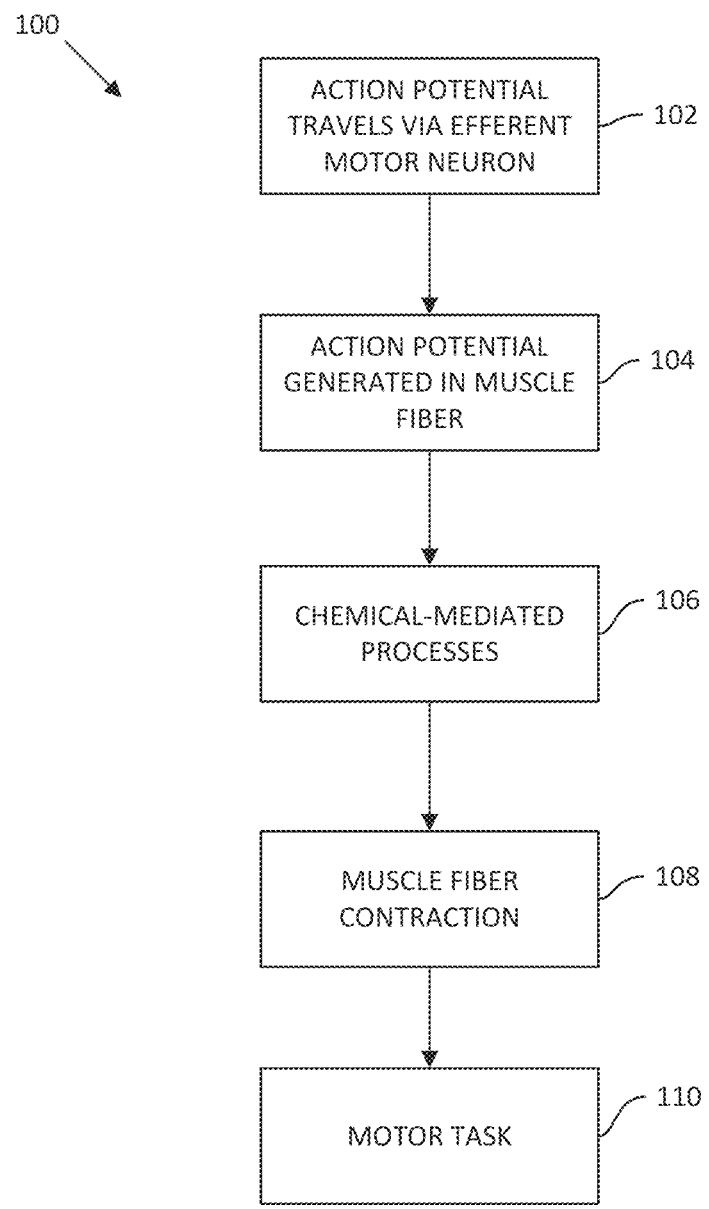
FIG. 1 is a flowchart of a biological process for performing a motor task in accordance with some embodiments of the technology described herein.

FIG. 1 illustrates a flowchart of a biological process 100 for initiating a motor task by the coordinated movement of one or more muscles. In act 102, action potentials are generated in one or more efferent spinal motor neurons. The motor neurons carry the neuronal signal (also referred to as "spikes" herein) away from the central nervous system and toward skeletal muscles in the periphery. For each motor neuron in which an action potential is generated, the action potential travels along the axon of the motor neuron from its body in the spinal cord where the action potential is generated to the axon terminals of the motor neuron that innervate muscle fibers included in skeletal muscles. A motor neuron and the muscle fibers that it innervates are referred to herein as a motor unit. Muscle fibers in a motor unit are activated together in response to an action potential generated in the corresponding motor neuron of the motor unit. Individual muscles typically include muscle fibers from hundreds of motor units with the simultaneous contraction of muscle fibers in many motor units resulting in muscle contraction evidenced as perceptible muscle movement and/or force.

A chemical synapse formed at the interface between an axon terminal of a spinal motor neuron and a muscle fiber is called a neuromuscular junction. As an action potential transmitted along the axon of a motor neuron reaches the neuromuscular junction, process 100 proceeds to act 104, where an action potential is generated in the muscle fiber as a result of chemical activity at the neuromuscular junction. In particular, acetylcholine released by the motor neuron diffuses across the neuromuscular junction and binds with receptors on the surface of the muscle fiber triggering a depolarization of the muscle fiber. Although neuromuscular signals sensed on the body surface generated by the depolarization of individual muscle fibers are small (e.g., less than 100 µV), the collective action of multiple muscle fibers conducting simultaneously results in a detectable voltage potential that may be recorded by neuromuscular (e.g., EMG) sensors located on the surface of the body. As noted above, the collective conduction of muscle fibers from many motor units results in muscle contraction and perceptible motion. Accordingly, when a user performs a movement or gesture, the corresponding recorded neuromuscular signals include contributions from multiple activated motor units.

Following generation of an action potential in the muscle fiber, process 100 proceeds to act 106, where the propagation of the action potential in the muscle fiber results in a series of chemical-mediated processes within the muscle fiber. For example, depolarization of a muscle fiber results in an influx of calcium ions into the muscle fiber. Calcium ions inside the muscle fiber bind with troponin complexes causing the troponin complexes to separate from myosin binding sites on actin filaments in the muscle fiber, thereby exposing the myosin binding sites.

Following these chemical-mediated processes, process 100 proceeds to act 108, where the muscle fiber contracts. Muscle fiber contraction is achieved due to the binding of exposed myosin heads with actin filaments in the muscle fiber creating cross-bridge structures. Process 100 then proceeds to act 110, where the collective contraction of muscle fibers in one or more muscles results in the performance of a motor task.

As the tension of a muscle increases, the firing rates of active motor neurons increases and additional motor neurons may become active, which is a process referred to as motor unit recruitment. The pattern by which motor neurons innervating a muscle become active and increase their firing rate is, in some cases, stereotyped. Some embodiments are directed to analyzing neuromuscular signals to detect and identify/classify spike events corresponding to firing of action potentials in one or more motor units.

When a user performs a motor task, such as moving their arm, a group of muscles necessary to perform the motor task is activated. When the motor task is performed while the user is wearing a wearable device that includes neuromuscular sensors (e.g., EMG sensors), the neuromuscular signals recorded by the sensors on the surface of the body correspond to superimposed activity of all motor units in the muscles in the group activated during performance of the motor task. The neuromuscular signals may be analyzed and mapped to control signals to control a device based on the type of movement or gesture that the user performs. In some embodiments, the analysis of neuromuscular signals involves the detection and identification of spike events in activated motor units.

A generative model of an EMG signal x(t) may take the form:

$$x(t) = \sum_{i}^{N} (s_i * t_i)(t) + \eta(t) \quad (1)$$

where t is the time, $s_i$ is the spatiotemporal waveform of the i-th MUAP observed by an EMG recording device, $t_i$ is the spike train of the corresponding motor neuron and $\eta(t)$ is the EMG measurement noise, where the spike train is represented as a time series of Dirac functions occurring each time the motor neuron fires.

As discussed above, a MUAP is an electrical potential generated by activation of muscle fibers in a corresponding motor unit. The spatiotemporal waveform of the MUAP as detected by a pair of EMG sensors (or a number of EMG sensors greater than two) depends primarily on the position of the motor unit relative to the array of EMG sensors. Tissue between the site of the muscle fiber(s) composing the motor unit and an EMG sensor filters the spatiotemporal waveform, so that the same EMG sensor (or EMG sensors) may measure a distinct spatiotemporal pattern due to different locations of the muscle fibers in the underlying tissue and, accordingly, unique filtering caused by tissue between the muscle fibers and an EMG sensor (or EMG sensors). Some embodiments assume that the spatiotemporal waveform of the MUAP remains constant as long as the electrode positions and the conductive medium (e.g., the user's body) do not change. In practice, small variations in the spatiotemporal waveform for a MUAP may be introduced due to muscle contractions. For surface EMG sensors, the duration of a MUAP is on the order of 10-20 ms and may have an amplitude on the order of hundreds of microvolts. The duration of the MUAP is influenced largely based on the spacing between differential EMG electrodes and the velocity of the action potential wave traveling along the muscle fibers. The amplitude of the MUAP is influenced largely based on the distance from the motor unit to the EMG electrode pair and the number of muscle fibers in the motor unit.

The inventors have recognized that since the spatiotemporal waveform of a MUAP remains substantially constant, and as such encodes little or no information related to user intent, some embodiments are directed to extracting spike event information (e.g., spike train data) from neuromuscular signals as a measure of user intent. The extracted spike event information may be used to generate one or more outputs (e.g., one or more control signals, where the control signals may be used to change the state of a computerized system that is configured to receive the control signal). A mapping between spike event information and control signals may be implemented, for example, using an inferential model trained to associate particular spike event information with control signal outputs. In some embodiments, the output of the trained inferential model may be musculoskeletal position information that describes, for example, the positions and/or forces of rigid body segments in a computer-implemented musculoskeletal model. As neuromuscular signals are continuously recorded and spike events detected, the musculoskeletal model may be updated with predictions of the musculoskeletal position information output from the inferential model. Control signals may then be generated based on the updated musculoskeletal position information. In other embodiments, the output of the trained inferential model may be the control signals themselves, such that a musculoskeletal model is not used. In other embodiments, spike event information from a plurality of motor units may be combined, for example to enable two-dimensional control.

As described in more detail below, some embodiments detect spike events in recorded neuromuscular signals and identify a biological source (e.g., a motor unit or group of motor units) of the detected spike events. The output (e.g., a control signal) is then generated based on the detected spike event(s) and/or the identified biological source.

Throughout this disclosure EMG sensors are used as examples of the type of neuromuscular sensors configured to detect neuromuscular activity. However it should be appreciated that other types of neuromuscular sensors including, but not limited to, mechanomyography (MMG) sensors and sonomyography (SMG) sensors may additionally or alternatively be used in combination with EMG sensors to detect neuromuscular activity in accordance with some embodiments. The neuromuscular signals recorded by the neuromuscular sensors may be used to identify activation of sub-muscular structures in accordance with the techniques described herein.

Figure 2:
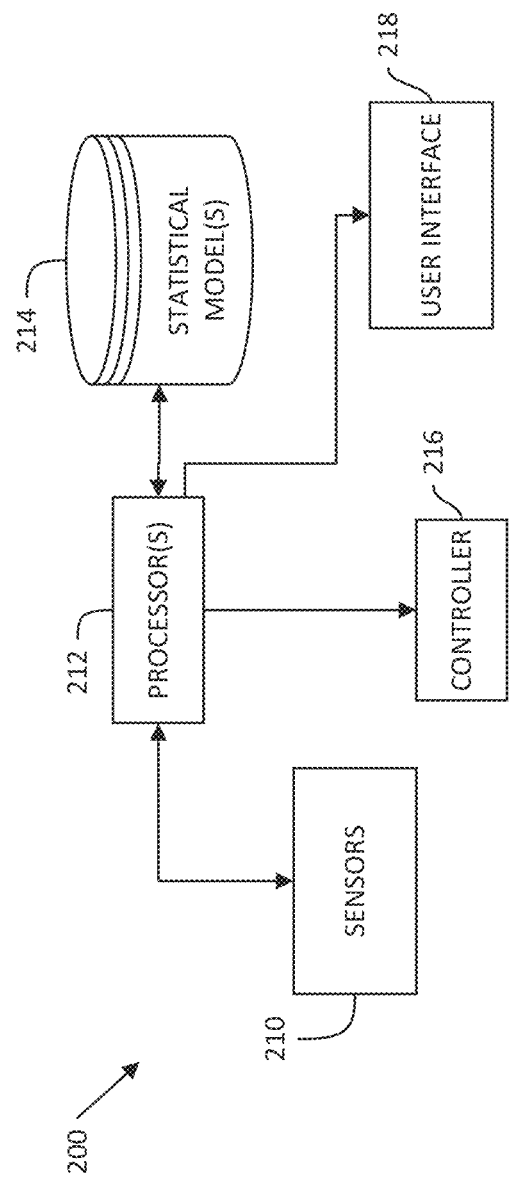
FIG. 2 is a schematic diagram of a computer-based system for detecting spike events in neuromuscular data in accordance with some embodiments of the technology described herein.

FIG. 2 illustrates a system 200 in accordance with some embodiments. The system includes a plurality of sensors 210 configured to record signals resulting from the activation of motor units with portions of a human body. Sensors 210 may include a plurality of neuromuscular sensors configured to record signals arising from neuromuscular activity in skeletal muscle of a human body, as described above. The term "neuromuscular activity" as used herein refers to neural activation of spinal motor neurons that innervate a muscle, muscle activation, muscle contraction, or any combination of the neural activation, muscle activation, and muscle contraction. In some embodiments, spike event information describing when an action potential has occurred and/or a biological source of a detected spike event may be determined from the sensed neuromuscular signals.

Sensors 210 may include one or more Inertial Measurement Units (IMUs), which measure a combination of physical aspects of motion, using, for example, an accelerometer, a gyroscope, a magnetometer, or any combination of one or more accelerometers, gyroscopes and magnetometers. In some embodiments, IMUs may be used to sense information about movement of the part of the body on which the IMU is attached and information derived from the sensed data (e.g., position and/or orientation information) may be tracked as the user moves over time. For example, one or more IMUs may be used to track movements of portions of a user's body proximal to the user's torso relative to the sensor (e.g., arms, legs) as the user moves over time. In some embodiments, signals from an IMU may be used to filter, post-process, or otherwise refine the spike event(s) inferred by an inferential model.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect motor unit activity within one or more body segments distal to the torso (e.g., a forearm or wrist). It should be appreciated, however, that the sensors may be arranged in any suitable way, and embodiments of the technology described herein are not limited based on the particular sensor arrangement. For example, in some embodiments, at least one IMU and a plurality of neuromuscular sensors may be co-located on a body segment to track motor unit activity and/or movements of the body segment using different types of measurements. In one implementation described in more detail below, an IMU sensor and a plurality of EMG sensors are arranged on a wearable device configured to be worn around the lower arm or wrist of a user. In such an arrangement, the IMU sensor may be configured to track movement information (e.g., positioning and/or orientation over time) associated with one or more arm segments, to determine, for example whether the user has raised or lowered their arm, whereas the EMG sensors may be configured to determine sub-muscular information associated with activation of sub-muscular structures in muscles of the wrist or hand. In some embodiments, an IMU sensor may provide control signals that a user may volitionally control independently from one or more MUAPs.

Each of the sensors 210 includes one or more sensing components configured to sense information about a user. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors), vibration sensors configured to measure skin surface vibrations (e.g., for MMG sensors), and acoustic sensing components configured to measure ultrasound signals (e.g., for SMG sensors) arising from muscle activity. Exemplary sensors 210 that may be used in accordance with some embodiments are described in more detail in U.S. patent application Ser. No. 15/659,018 entitled "METHODS AND APPARATUS FOR PREDICTING MUSCULO-SKELETAL POSITION INFORMATION USING WEARABLE AUTONOMOUS SENSORS," incorporated by reference herein by its entirety.

In some embodiments, at least some of the plurality of sensors are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively, at least some of the sensors may be arranged on a wearable patch configured to be affixed to a portion of the user's body, at least some of the sensors may be implanted EMG sensors, or at least some of the sensors may be included as a portion of an electronic tattoo worn by the user. In some embodiments, multiple wearable devices, each having one or more neuromuscular sensors (and, optionally, one or more IMUs) included thereon may be used to generate control information based on MUAPs, sub-muscular structures, and/or movement that involve multiple parts of the body.

Figure 6:
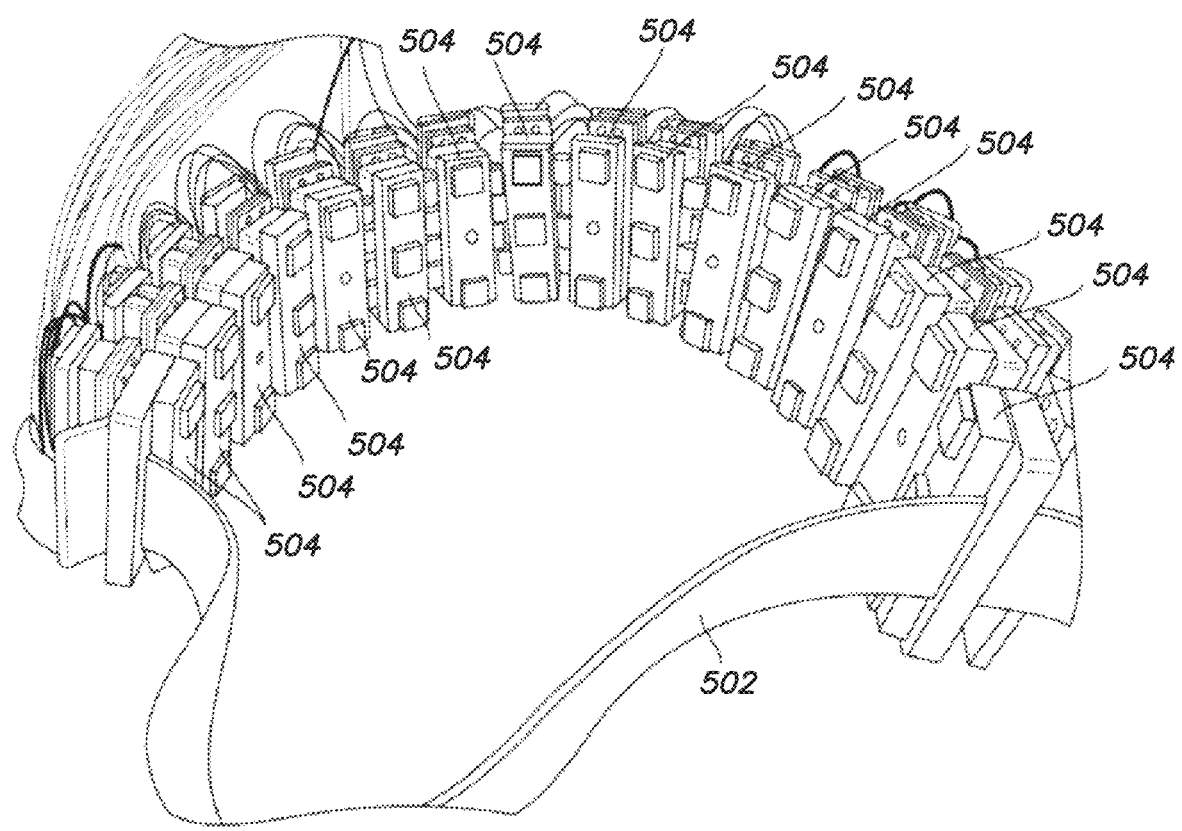
FIG. 6 illustrates a wristband having EMG sensors arranged circumferentially thereon, in accordance with some embodiments of the technology described herein.
Figure 7:
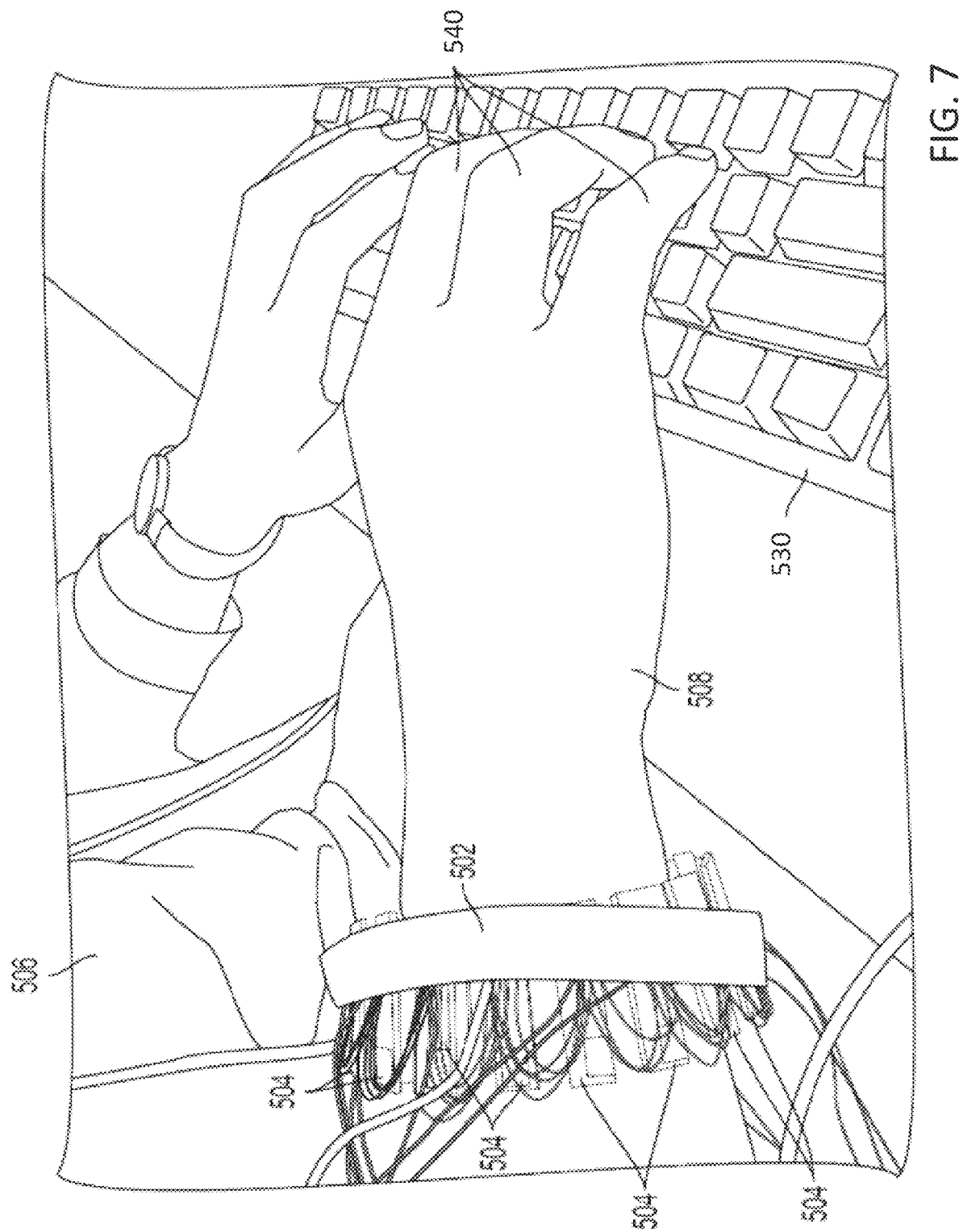
FIG. 7 illustrates a user wearing the wristband of FIG. 6 while typing on a keyboard, in accordance with some embodiments of the technology described herein.

In one implementation, sixteen EMG sensors are arranged circumferentially around an elastic band configured to be worn around a user's lower arm. For example, FIG. 6 shows EMG sensors 504 arranged circumferentially around elastic band 502. It should be appreciated that any suitable number of neuromuscular sensors may be used and the number and arrangement of neuromuscular sensors used may depend on the particular application for which the wearable device is used. It should also be appreciated that the neuromuscular sensors may be placed on (or implanted in) any part of the body. For example, a wearable armband or wristband may be used to generate control information for controlling a robot, controlling a vehicle, scrolling through text, controlling a virtual avatar, activating a discrete control (e.g. a button), navigating in a two-dimensional (or higher dimensional) space, or any other suitable control task. For example, as shown in FIG. 7, a user 506 may be wearing elastic band 502 on hand 508. In this way, EMG sensors 504 may be configured to record EMG signals as a user controls keyboard 530 using fingers 540. In some embodiments, elastic band 502 may also include, as an option, one or more IMUs (not shown), configured to record movement information, as discussed above. In other embodiments, the wearable device may be provided without an IMU.

In some embodiments, multiple wearable devices, each having one or more IMUs and/or neuromuscular sensors included thereon may be used to generate control information based on MUAPs, activation associated with sub-muscular structures, and/or movement that involve multiple parts of the body.

In some embodiments, sensors 210 only include a plurality of neuromuscular sensors (e.g., EMG sensors). In other embodiments, sensors 210 include a plurality of neuromuscular sensors and at least one "auxiliary" sensor configured to continuously record a plurality of auxiliary signals. Examples of auxiliary sensors include, but are not limited to, IMU sensors, an imaging device (e.g., a camera), a radiation-based sensor for use with a radiation-generation device (e.g., a laser-scanning device), or other types of sensors such as a heart-rate monitor.

In some embodiments, the output of one or more of the sensing components may be optionally processed using hardware signal processing circuitry (e.g., to perform amplification, filtering, and/or rectification). In other embodiments, at least some signal processing of the output of the sensing components may be performed in software. Accordingly, signal processing of signals recorded by the sensors may be performed in hardware, software, or by any suitable combination of hardware and software, as aspects of the technology described herein are not limited in this respect.

In some embodiments, the recorded sensor data may be optionally processed to compute additional derived measurements that are then provided as input to a spike event detection process. For example, recorded signals from an IMU sensor may be processed to derive an orientation signal that specifies the orientation of a body segment over time. In another example, recorded signals from an IMU sensor may be processed to determine movement (e.g. high velocity movement) that may cause sensor movement artifacts or shifts in the spatial location of muscle fibers of a motor unit relative to one or more EMG sensors, each of which may cause spurious spike events to be detected. Accordingly, IMU sensor data may be used to filter or otherwise refine the output of an inferential model configured for detecting one or more MUAPs. Sensors may implement signal processing using components integrated with the sensing components, or at least a portion of the signal processing may be performed by one or more components in communication with, but not directly integrated with the sensing components of the sensors 210.

System 200 also includes one or more computer processors 212 programmed to communicate with sensors 210. For example, signals recorded by one or more of the sensors may be provided to the processor(s) 212, which may be programmed to execute one or more machine learning algorithms that process signals output by the sensors 210 to train one or more inferential models (e.g., statistical models 214), and the trained (or retrained) statistical model(s) 214 may be stored for later use in generating control signals, as described in more detail below.

In some embodiments, statistical model 214 may be a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be a fully recurrent neural network, a gated recurrent neural network, a recursive neural network, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used.

In some embodiments, the output of an inferential model (e.g., a statistical model) provides discrete outputs. Discrete outputs (e.g., classification labels) may be used, for example, when a desired output is to know whether a particular pattern of activation (including individual neural spiking events) is detected in the neuromuscular signals. For example, the model may be trained to estimate whether the user is activating a particular motor unit, activating a particular motor unit with a particular timing, activating a particular motor unit with a particular firing pattern, or activating a particular combination of motor units. On a shorter timescale, discrete classification is used in some embodiments to estimate whether a particular motor unit fired an action potential within a given amount of time. In such a scenario, these estimates may then be accumulated to obtain an estimated firing rate for that motor unit.

In embodiments in which the statistical model is implemented as a neural network configured to output a discrete signal, the neural network may include a softmax layer such that the outputs add up to one and may be interpreted as probabilities. The output of the softmax layer may be a set of values corresponding to a respective set of control signals, with each value indicating a probability that the user wants to perform a particular control action. As one non-limiting example, the output of the softmax layer may be a set of three probabilities (e.g., 0.92, 0.05, and 0.03) indicating the respective probabilities that the detected pattern of activity is one of three known patterns.

It should be appreciated that when the statistical model is a neural network configured to output a discrete signal, the neural network is not required to produce outputs that add up to one. For example, instead of a softmax layer, the output layer of the neural network may be a sigmoid layer (which has no restriction that the probabilities add up to one). In such embodiments, the neural network may be trained with a sigmoid cross-entropy cost. Such an implementation may be advantageous in the case when multiple different control actions may occur within a threshold amount of time and it is not important to distinguish the order in which these actions occur (e.g., a user may activate two patterns of neural activity within the threshold amount of time). In some embodiments, any other suitable non-probabilistic multi-class classifier may be used, as aspects of the technology described herein are not limited in this respect.

In some embodiments, the output of the statistical model may be a continuous signal rather than a discrete signal. For example, the model may output an estimate of the firing rate of each motor unit or the model may output a time-series electrical signal corresponding to each motor unit or sub-muscular structure.

It should be appreciated that aspects of the technology described herein are not limited to using neural networks, as other types of statistical models may be employed in some embodiments. For example, in some embodiments, the statistical model may comprise a hidden Markov model (HMM), a switching HMM with the switching allowing for toggling among different dynamic systems, dynamic Bayesian networks, and/or any other suitable graphical model having a temporal component. Any such statistical model may be trained using recorded sensor signals.

As another example, in some embodiments, the statistical model is a classifier taking as input, features derived from the recorded sensor signals. In such embodiments, the classifier may be trained using features extracted from the sensor data. The classifier may be a support vector machine, a Gaussian mixture model, a regression based classifier, a decision tree classifier, a Bayesian classifier, and/or any other suitable classifier, as aspects of the technology described herein are not limited in this respect. Input features to be provided to the classifier may be derived from the sensor data in any suitable way. For example, the sensor data may be analyzed as time series data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor data may be transformed using a wavelet transform and the resulting wavelet coefficients may be provided as inputs to the classifier.

In some embodiments, values for parameters of the statistical model may be estimated from training data. For example, when the statistical model is a neural network, parameters of the neural network (e.g., weights) may be estimated from the training data. In some embodiments, parameters of the statistical model may be estimated using gradient descent, stochastic gradient descent, and/or any other suitable iterative optimization technique. In embodiments where the statistical model is a recurrent neural network (e.g., an LSTM), the statistical model may be trained using stochastic gradient descent and backpropagation through time. The training may employ a cross-entropy loss function and/or any other suitable loss function, as aspects of the technology described herein are not limited in this respect.

System 200 also optionally includes one or more controllers 216. For example, controller 216 may be a display controller configured to display a visual representation (e.g., of a hand) on a display. As discussed in more detail below, one or more computer processors may implement one or more trained statistical models that receive as input sensor signals and provide as output information that is used to generate control signals.

In some embodiments, a computer application configured to simulate a virtual reality environment may be instructed to display a visual character such as an avatar (e.g., via controller 216). Positioning, movement, and/or forces applied by portions of visual character within the virtual reality environment may be displayed based on the output of the trained statistical model(s). The visual representation may be dynamically updated as continuous signals are recorded by the sensors 210 and processed by the trained statistical model(s) 104 to provide a computer-generated representation of the character's movement that is updated in real-time.

Some embodiments are directed to using a statistical model, at least in part, to map spike event information extracted from the neuromuscular signals to control signals. The statistical model may receive as input IMU signals, neuromuscular signals (e.g., EMG, MMG, and/or SMG signals), spike event information (e.g., spike train data) extracted from neuromuscular signals, external device signals (e.g., camera or laser-scanning signals), or a combination of IMU signals, neuromuscular signals, and external device signals detected as a user performs one or more muscular activations. In some embodiments, the statistical model may be used to predict the control information without the user having to make perceptible movements.

System 200 also optionally includes a user interface 218. Feedback determined based on the signals recorded by sensors 210 and processed by processor(s) 212 may be provided via user interface 218 to facilitate a user's understanding of how the system is interpreting the user's intended activation. User interface 218 may be implemented in any suitable way including, but not limited to, an audio interface, a video interface, a tactile interface, and electrical stimulation interface, or any combination of the foregoing. In general, control signals based on a user activating one or more MUAPs may require user training so that the user may effectively and reliably activate the intended one or more MUAPs to create intended control signals. In general, a user cannot detect the activation of a single MUAP, because the amount of force exerted by the muscle is below the detection limit of the proprioceptive system. In some embodiments of the invention, systems and methods provide sensory feedback to a user when they have activated a specified (i.e. desired) MUAP (and a model has detected the presence of the specified MUAP), so that the user may become more skillful at reliably activating that MUAP. For example, feedback may comprise auditory, visual, haptic, or multi-sensory feedback with sufficiently low latency for the user to learn the mapping between the sensory feedback and the preceding MUAP activation.

The architecture of system 200 may take any suitable form. Some embodiments employ a thin architecture in which processor 212 is included as a portion of a device separate from and in communication with the plurality of neuromuscular sensors 210 arranged on the one or more wearable devices. The neuromuscular sensors may be configured to wirelessly stream in substantially real-time, the plurality of neuromuscular signals and/or the information derived from the plurality of neuromuscular signals to processor 212 for processing including, but not limited to, spike event detection and biological source identification. The device separate from and in communication with the plurality of neuromuscular sensors may be, for example, a remote server, a desktop computer, a laptop computer, a smartphone, or a wearable electronic device such as a smartwatch, a health monitoring device, smart glasses, other wearable system (including head mounted wearable systems), or an augmented reality system.

Some embodiments employ a thick architecture in which processor 212 is integrated with the one or more wearable devices on which the neuromuscular sensors 210 are arranged. In yet further embodiments, the processing for spike event detection and/or biological source identification is divided between multiple processors, at least one of which is integrated with sensors 210 and at least one of which is included as a portion of a device separate from and in communication with the sensors 210. In such an implementation, the neuromuscular sensors may be configured to transmit at least some of the recorded neuromuscular signals to a first computer processor remotely located from the sensors. The first computer processor may be programmed to train, based on the transmitted neuromuscular signals, at least one spike detection model and/or at least one spike identification model. The first computer processor may then be programmed to transmit the trained at least one spike detection model and/or the at least one spike identification model to a second computer processor integrated with the one or more wearable devices on which the sensors are arranged. The second computer processor may be programmed to detect spike events and determine the biological source of the detected spike events using the at least one spike detection model and/or the at least one spike identification model transmitted from the first computer processor. In this way, the training/fitting process and the real-time process of using the trained model(s) may be separated by being performed by different processors.

Figure 3:
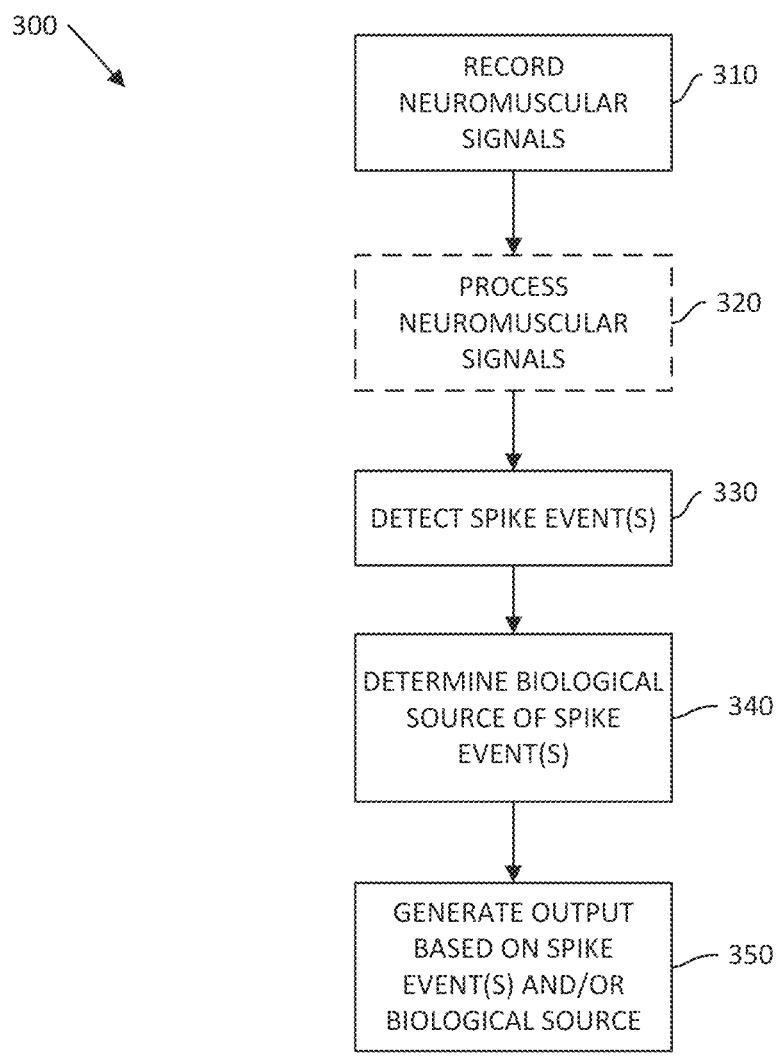
FIG. 3 is a flowchart of a substantially real-time process for detecting spike event information from neuromuscular data in accordance with some embodiments of the technology described herein.

FIG. 3 illustrates a process 300 for generating an output based on one or more spike events detected in recorded neuromuscular signals in accordance with some embodiments. In act 310, a plurality of neuromuscular signals are recorded by a plurality of neuromuscular sensors worn by a user as the user activates one or more motor units. Process 300 then proceeds to act 320 where the recorded neuromuscular signals are optionally processed prior to detection of spike events. For example, one or more time-lagged versions of the recorded signals may be generated and the time-lagged versions may subsequently be used for detection of spike events. The inventors have recognized that effective time lag values are on the order of the timescale of a motor unit action potential with the particular neuromuscular recording technique employed. For example, the motor unit action potentials measured using surface EMG recordings generally exhibit a time lag in a range of between 10 and 50 ms. In some embodiments, a time lag of 15 to 25 ms may also be effective.

Process 300 then proceeds to act 330, where at least one spike event is detected in the recorded neuromuscular signals. For example, in some embodiments, the recorded neuromuscular signals or information derived from the recorded neuromuscular signals (e.g., time-lagged versions of the recorded neuromuscular signals) are processed using one or more filters to detect spike events in the recorded neuromuscular signals. In some embodiments, the one or more filters includes a plurality of filters, each of which is configured to detect spikes generated from a particular biological source (e.g., from a particular motor unit). Example techniques for generating filters for use with some embodiments are described in more detail below.

Process 300 then proceeds to act 340, where the biological source of the detected spike event(s) is determined. In embodiments that use a plurality of filters, each of which is configured to detect spike events generated by a particular biological source, the biological source determination in act 340 may be based on the output of the plurality of filters and their associated biological sources for which they are configured to detect spike events. In other embodiments, the detection of one or more spike events in act 330 and the determination of a biological source of the spike event(s) in act 340 may be performed sequentially. Any suitable biological source for spike events may be determined in act 340. For example, the biological source may be a single motor unit, a group of motor units, a muscle, or a group of muscles. In some embodiments, the ability of the system to determine a particular biological source for spike events may be based, at least in part, on a spatiotemporal resolution of the system in distinguishing between different spike events. For example, in some instances the system may not be able to determine which of a plurality of motor units a spike originated from, but the system may be able to determine a group of motor units from which the spike originated. In other instances, the system may not be able to determine within a muscle which of the motor units a spike originated from, but the system may be able to determine which muscle the spike originated from, and so on.

Process 300 then proceeds to act 350, where one or more outputs are generated based on the detected spike event(s) and/or the biological source of the spike event(s). Any suitable output may be generated for a particular application, and embodiments are not limited in this respect. In some embodiments, the output may be compressed data representing the recorded neuromuscular signals. For example, rather than storing "raw" neuromuscular signals, the system may be configured to store only information about the detected spike events such as their timing characteristics and/or their biological source information. Storing such compressed data may be beneficial, for example, for transmission of the data (e.g., over one or more wireless networks) to an external device and/or for logging data for health/fitness/ergonomics monitoring applications without having to store the raw recorded data.

In some embodiments, the output generated in act 350 is information used to update a musculoskeletal model. As described briefly above, some embodiments employ a musculoskeletal model that is updated with musculoskeletal position information describing, for example, positions and/or forces of rigid body segments in the model. Spike event information determined in acts 330 and/or 340 may be provided as input to the musculoskeletal model as part of the updating process. Control signals may then be generated based on the updated musculoskeletal model.

In some embodiments, the output generated in act 350 is a control signal used to control an external device. Rather than mapping recorded neuromuscular signals directly to control signals using, for example, a trained statistical model, some embodiments map spike event information (e.g., detected spike events and/or biological source information for the spike events) to control signals. In such an implementation, one or more control signals may be generated based on the identified biological source(s) and a pattern of activation represented in the detected spike event information. For example, the spike event information may be provided as input to a trained statistical model and an output of the trained statistical model may be used to generate the one or more control signals. In one implementation, the output of the trained statistical model may be a set of one or more control signals. In another implementation, the control signal(s) may be generated based on the spike event information without the use of a trained statistical model. The generated control signal(s) may then be provided to a control interface of a device to control an operation of the device. For example, the device may be a display and a control signal may be provided to a display controller of the display. The control signal may include instructions to update information displayed on the display. Alternatively the device may be a computer or other computing device (e.g., a smartphone) and the control signal may be provided to a controller of the computing device to change an operation of the device. In yet a further example, the control signal may be used to control a device (e.g., a musical instrument) to provide an artistic expression. It should be appreciated that any device having a control interface may be controlled using control systems designed in accordance with the techniques described herein.

In some embodiments, the one or more control signals are generated based, at least in part, on the spike event information in substantially real-time. As used herein the term "substantially real-time" means that the spike event information determination process occurs and/or the control signals are generated shortly after the electrical event occurs while the neuromuscular data is being recorded, rather than happening off-line at a time when the neuromuscular signals are not being recorded. In some embodiments, spike event information is detected within 5 seconds, within 1 second, within 500 ms, within 100 ms, or within 50 ms of the occurrence of the electrical event.

The spike event information used to generate output in act 350 may include information about the spatiotemporal pattern of detected spike events (e.g., spike rate, spatial distribution of spike events, biological source of spike events). In some embodiments, one or more control signals may be generated based, at least in part, on at least one characteristic of the spatiotemporal pattern of the detected spike events. For example, the one or more control signals may be generated based, at least in part, on a spike rate and/or a spatial distribution of spike events detected from the neuromuscular signals.

In general, control signals based on MUAPs from one or more motor units may be used as one or more discrete controls (i.e. a button or set of buttons that, when activated cause a computing device to change an operation), one or more continuous controls (i.e. a one-dimensional controller such as to control the volume of a speaker or the temperature of a thermostat, a two-dimensional controller such as to navigate a cursor on a two-dimensional screen, or a higher-dimensional controller such as to control a robotic arm with three or more degrees of freedom). In some embodiments, control signals based on MUAPs may comprise composite controls based on a particular sequence of activation of one or more MUAPs in order to achieve a greater number of discrete controls (i.e. degrees of freedom (DOF)) than the number of MUAPs identified. In an alternative or complementary embodiment for achieving a greater number of discrete controls (i.e. DOFs), a user may simultaneously (or near-simultaneously, within a defined period of time) activate two or more MUAPs that achieve unique discrete controls than the unitary activation of a MUAP. One skilled in the art will recognize that continuous controls as described above are generally not truly continuous and represent quantized control across a range of values.

Figure 4:
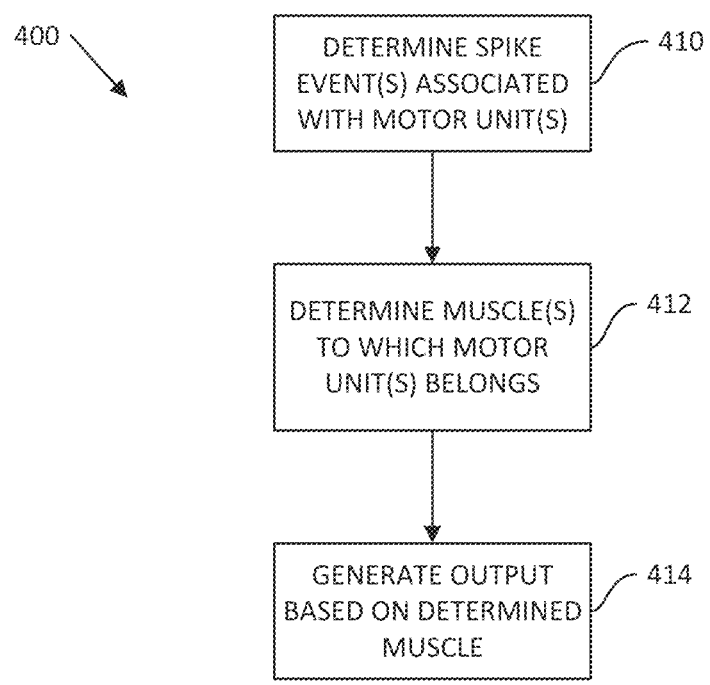
FIG. 4 is a flowchart of a process for associating spike events with muscles in accordance with some embodiments of the technology described herein.

In some embodiments, the motor unit(s) from which a detected spike event(s) originated from may be mapped to one or more muscles. FIG. 4 illustrates a process 400 for performing muscle classification in accordance with some embodiments. In act 410, spike event information is determined, for example, in accordance with at least a portion of process 300 described above. Process 400 then proceeds to act 410, where one or more muscles to which the identified motor unit belongs is determined. The muscle(s) may be determined in any suitable way. For example, similarities between spatial profiles and correlations in spiking activity arising from multiple motor units may indicate that the multiple motor units belong to the same muscle. Alternatively, the muscular (or sub-muscular) source may be inferred based on the spatial pattern of signals recorded on a plurality of neuromuscular sensors on the skin of a user (or, optionally, implanted in a user). Process 400 then proceeds to act 414, where output is generated based, at least in part, on the determined muscle associated with the spike event information. In some embodiments, the identification of a particular muscle relating to detected spike events may be used to further describe information about the spike events relative to the identified muscle. For example, as described above, each muscle in the human body may be characterized by a particular pattern of motor unit recruitment that describes an order by which additional motor units are recruited when needed. In some embodiments, the information about a motor unit recruitment pattern of a muscle may be used, at least in part, to determine where the motor unit or group of motor units falls within the motor unit recruitment pattern for the determined muscle.

Figure 5:
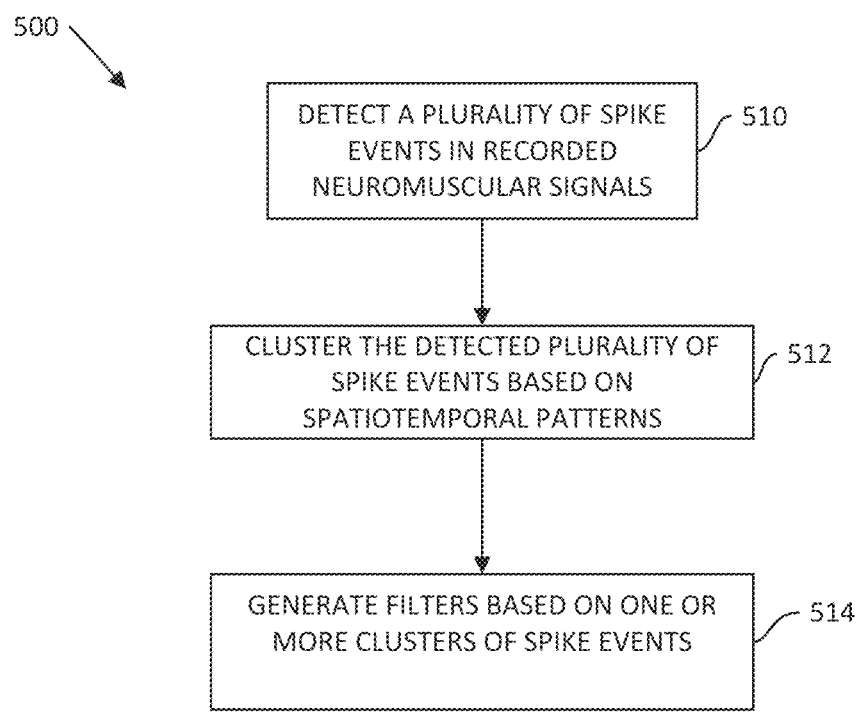
FIG. 5 is a flowchart of a process for generating filters for use with a substantially real-time spike event decoder in accordance with some embodiments of the technology described herein.
Figure 8:
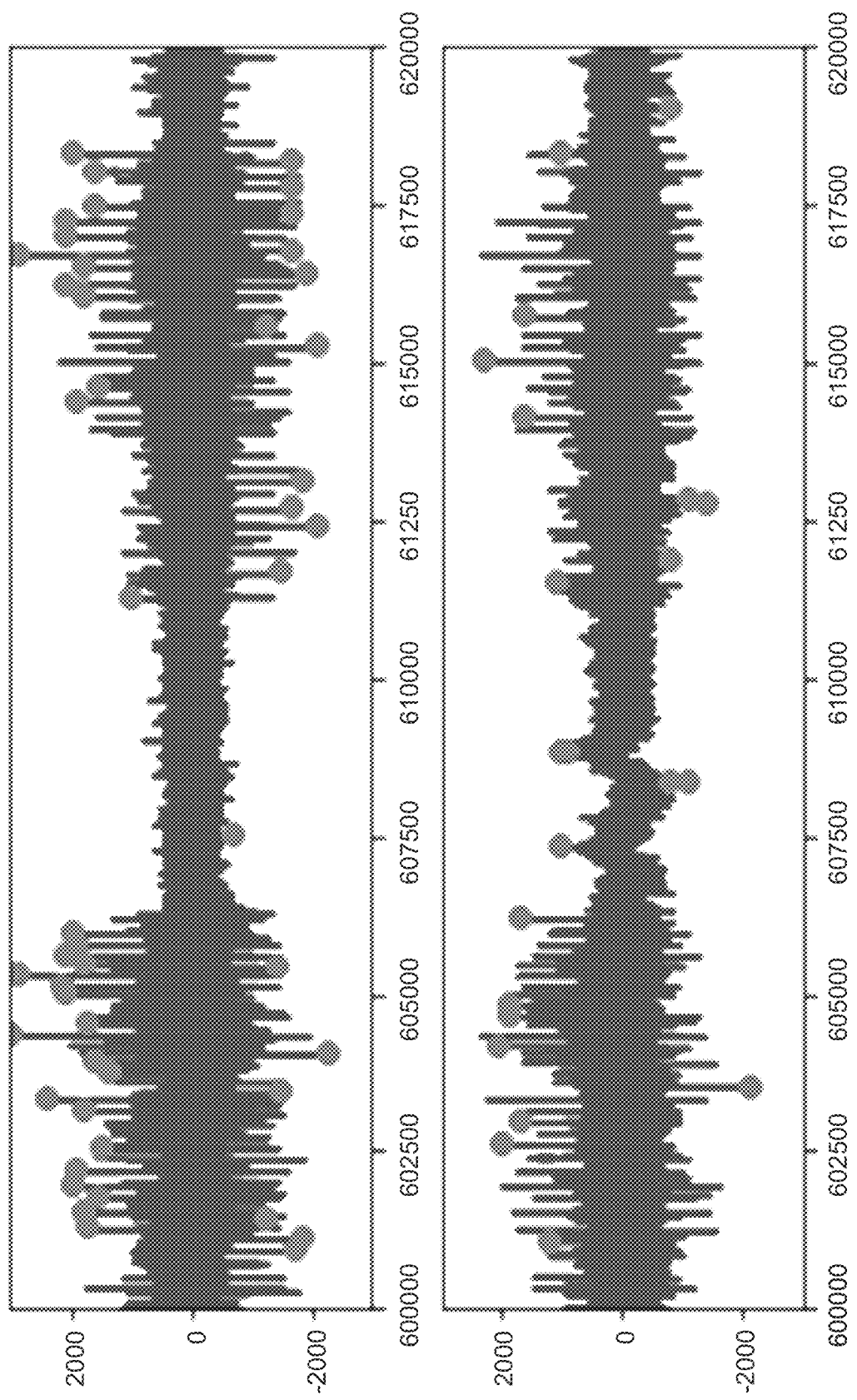
FIG. 8 illustrates a plot for detecting spike events in two channels of recorded neuromuscular data during periods of low activity, in accordance with some embodiments of the technology described herein.

Some embodiments are directed to a process for generating one or more filters used to decode spike events from recorded neuromuscular signals. FIG. 5 illustrates a process 500 for generating a plurality of filters, each of which represents spike activity within a biological source (e.g., a motor unit). The plurality of filters, once generated, may be used to process neuromuscular signals and provide outputs in substantially real-time as the neuromuscular signals are recorded. Additionally, in some embodiments, as additional neuromuscular data is recorded, filter parameters may be updated such that the filters are dynamically updated. In act 510, a plurality of spike events are detected in recorded neuromuscular signals. For example, neuromuscular signals may be recorded during periods of relatively low activity, and then spike events may be detected using thresholding of the recorded data. FIG. 8 shows an example of the detection of putative spike events in two EMG sensor channels during periods of low activity. The putative spike events detected in the EMG recordings may be analyzed to eliminate false positives. For example, putative spike events having one or more particular characteristics (e.g., a duration longer than a threshold duration) may be discarded.

Figure 9A:
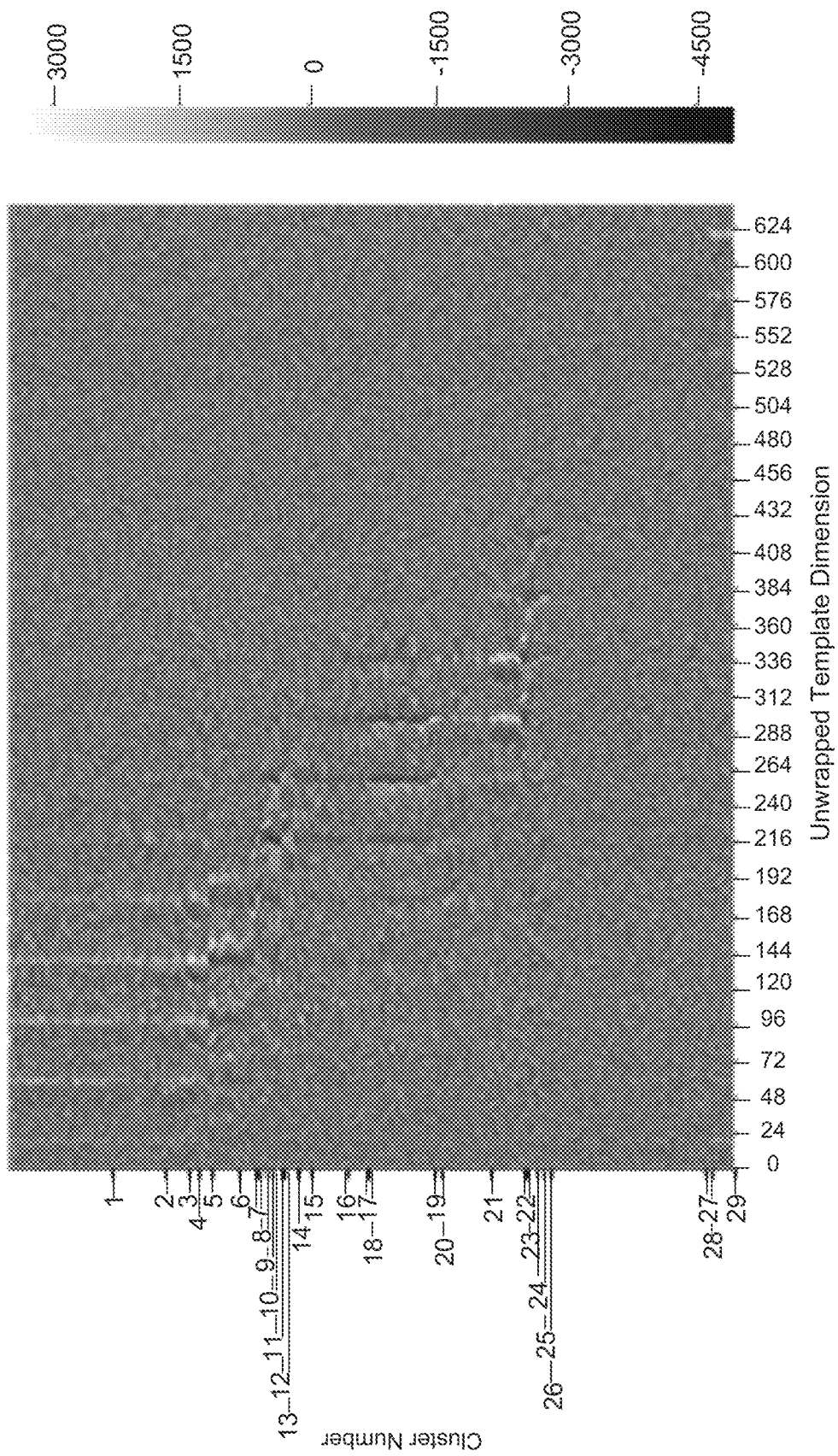
FIG. 9A is a color figure illustrating a plot of clustering spike events to identify spike events with similar spatiotemporal profiles, in accordance with some embodiments of the technology described herein.

After the plurality of spike events have been detected, process 500 proceeds to act 512, where the detected spike events are clustered, based on their spatiotemporal characteristics, to identify spike events likely arising from the same biological source. Clustering of spike events may occur in any suitable way. In one simplistic example of clustering, a window (e.g., a 10 ms window) around each of the peaks of the spike events may be used to define the temporal bounds of the event. Each spike event may then be defined as a vector of values, where each vector includes N×M samples, where N corresponds to the number of samples in the window for the event, and M corresponds to the number of neuromuscular sensors. For example, if the sampling rate of the neuromuscular data is 4 kHz, and the window for each spike event is 10 ms, N=40. Assuming an array of 15 neuromuscular sensors, the number of values in each spike event vector would be 40*15=600 values. After defining vectors for all of the detected spike events, a similarity metric may be used to identify vectors having values that cluster together, and thus are likely to represent spike events generated from a common biological source. For example, Principal Component Analysis (PCA) or some other suitable technique may be used to reduce the dimensionality of each of the spike event vectors, and k-means clustering or another suitable clustering technique may be used to cluster the lower-dimensional vectors into clusters of spike waveforms that have similar spatiotemporal characteristics. Other non-limiting examples of dimensionality reduction techniques include t-Distributed Stochastic Neighbor Embedding, deep auto-encoders, and Uniform Manifold Approximation and Projection (UMAP). Other non-limiting examples of clustering methods include agglomerative clustering, Density-Based Spatial Clustering of Applications with Noise (DB-SCAN), Hierarchical Density-Based Spatial Clustering of Applications with Noise (HDBSCAN). In another example, the vectors for each of the spike events are used to create an affinity matrix of the different spike events and a measure of similarity of the vectors, for example, using correlations, may be used to identify the clusters of spike waveforms having similar spatiotemporal characteristics. FIG. 9A illustrates the results of a clustering process in which clusters of spike waveforms having similar spatiotemporal characteristics have been identified.

Figure 9B:
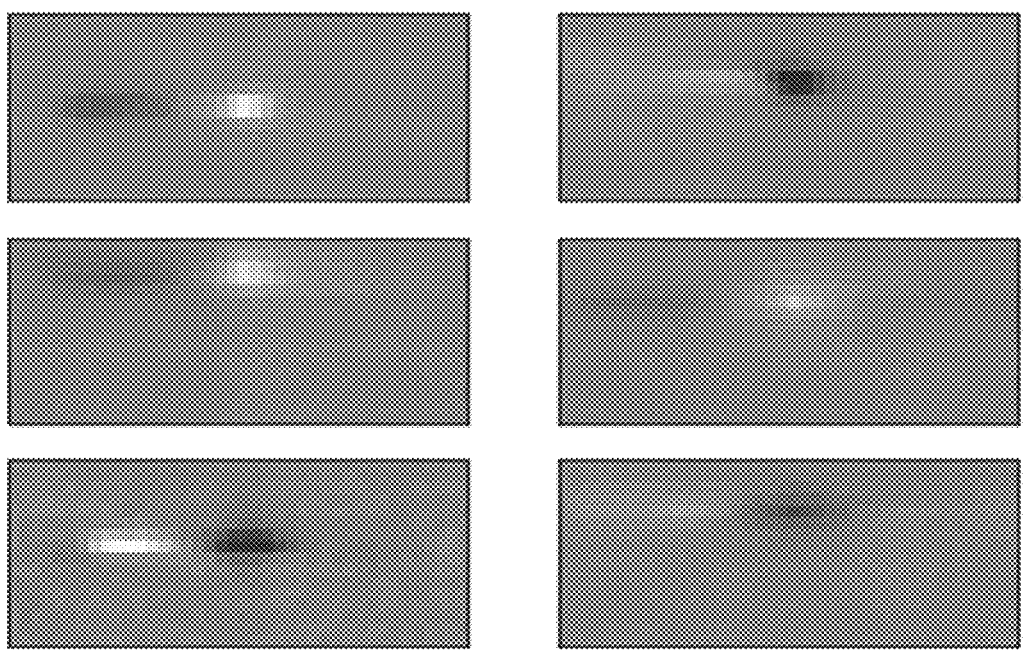
FIG. 9B is a color figure illustrating six spatiotemporal profiles generated for each of six clusters of spike events, in accordance with some embodiments of the technology described herein.

Each of the clusters of spike event data includes a plurality of spike events that represent a distribution of spike events generated by a particular biological source (e.g., a motor unit). The process then proceeds to act 514, where a plurality of filters are generated based on the spike events within each of the clusters, resulting in a set of filters, each of which is configured to detect spike events for its associated biological source (i.e., MUAP spike event). Act 512 serves to produce labeled spike event data from the unlabeled data detected in act 510. The labeled spike event data from act 512 may then be used, at least in part, to generate filters in act 514. In some embodiments, the spatiotemporal response function for each cluster may be determined by, for example, calculating the mean of each of the spike event vectors in the cluster. FIG. 9B illustrates example spatiotemporal profiles calculated for six clusters using this technique. The spatiotemporal profiles may then be used to generate the filters in act 514. For example, some embodiments use a beamforming formulation to determine filters for automatic spike decoding. An example of a beamforming formulation that may be used to generate filters in accordance with some embodiments is the minimum variance distortionless response (MVDR) filter, described in more detail below. In some embodiments, multiple filters may be used to disambiguate multiple motor units that are present in one cluster, such as motor units that are located near each other anatomically. For instance, multiple MVDR filters may be combined to disambiguate multiple motor units that are present in one MVDR cluster.

Instead of using filters to perform automatic spike event detection from neuromuscular data, some embodiments employ neural networks to detect spike event data, and the labeled data output from act 512 in process 500 may be used to train the neural network. Any suitable neural network architecture may be used including, but not limited to, convolutional neural networks and recurrent neural networks. When recurrent neural networks are used, a convolutional layer may be used as the first layer of the network.

Beamforming methods use filters to determine source signals from multidimensional sensor signals. Beamforming methods commonly use purely spatial filters. However, the inventors have recognized that spatial filtering alone is not suitable for detecting spike events in neuromuscular signals due to the large number of similarly localized sources relative to the small number of sensor channels. Accordingly, some embodiments use a time-lagged representation of the recorded neuromuscular signals to increase their effective dimensionality and exploit the consistent spatiotemporal response function for each source. Any suitable beamforming technique may be used, examples of which include, but are not limited to MVDR, described in more detail below, and linear constrained minimum variance (LCMV), according to which the filters weights are $W=(L^T C^{-1} L)^{-1} L^T C^{-1}$, where L is the matrix of spatiotemporal response profiles (i.e. the collection of all h vectors in the MVDR notation below) and C is the sensor signal covariance matrix (equivalent to $\phi_{yy}$ in the MVDR notation below). The outputs of the filtered signals may then be thresholded to determine whether a spike event occurs. Each filter corresponds to a biological source (e.g., an individual motor unit), so spike detection and identification of the spike's biological source occur as a single process.

Some embodiments are directed to using a plurality of MVDR filters to perform real-time spike detection in neuromuscular signals. Similar to matched filtering, the use of MVDR filters maintains a target signal as much as possible, but also minimizes the noise of any other signals that are present in the recorded neuromuscular signals. Assuming S sources, each of which has a stereotyped signal profile or template across channels and time, let $x_s(t)$ be a binary variable indicating whether source s is triggered at time t. $x_s(t)$ will have a value of 1 for only a single time step at a time, not for the duration of the emission. Let $h_{sc}(\tau)$ be the profile of the stereotyped profile of source s as measured in channel c at time $\tau$. Then the measured signal will be $y_c(t)=(\Sigma_s h_{sc}(t)*x_s(t)+n_c(t)=\Sigma_s\Sigma_\tau h_{sc}(t-\tau)x_s(t)+n_c(t))$, where * is the convolution operator and $n_c(t)$ is additional noise on channel c at time t. In order to make the derivation more mathematically straightforward, y, x, and h may be unwrapped into time-lagged vectors for each time-step. The template, instead of being a 2D matrix of size C×T for C channels and T timesteps, is unwrapped into a CT×1 vector, which is equivalent to concatenating successive time frames of the template on top of each other. The stacked template is then $h_s=[h_s(0),h_{s1}(0), h_{s2}(0), \ldots, h_{sC-1}(0), h_{s0}(1), \ldots h_{sC-1}(T-1)]^T$. The stacked observation is $y(t)=[y_0(t),y_1(t),y_2(t), \ldots, y_{C-1}(t),y_0(t+1), \ldots y_{C-1}(t+T-1)]^T$ and the stacked noise is $n(t)=[n_0(t),n_1(t),n_2(t), \ldots, n_{C-1}(t),n_0(t+1), \ldots n_{C-1}(t+T-1)]^T$. Then the model can be rewritten as $y(t)=\Sigma_s h_s x_s(t)+n(t)$. Assuming a single source of interest, then $y(t)=hx(t)+n(t)$. To find a filter, w that can be applied to $y(t)$ recover $x(t)$, the estimate of which may be provided as $\hat{x}(t)=w^T y(t)=w^T(hx(t)+n(t))$. The MVDR filter is the filter $\hat{w}$ that satisfies the following optimization $\hat{w}=\min_w E[\hat{x}^2]$, such that $w^T h=1$. Manipulating the term $E[\hat{x}^2]$ yields $E[\hat{x}^2]=E[(w^T y(t))^2]=E[(w^T y(t) y^T(t)w)]=w^T E[y(t)y^T(t)]w=w^T \phi_{yy} w$, where $\phi_{yy}$ is the correlation matrix for all of the entries of y. Thus, the optimization becomes $\hat{w}=\min_w w^T \phi_{yy} w$, such that $w^T h=1$. This problem has a closed-form solution, which is $$\hat{w} = \frac{\phi_{yy}^{-1} h}{h^T \phi_{yy}^{-1} h}.$$

To compute this filter, an estimate of the template h and the covariance of the observation $\phi_{yy}$ is required. In some embodiments, $\phi_{yy}$ is computed as the sample covariance matrix from the observation. The estimated signal is then $$\hat{x}(t) = w^T(hx(t) + n(t)) = \frac{h^T \phi_{yy}^{-1}}{h^T \phi_{yy}^{-1} h}(hx(t) + n(t)) = x(t) \frac{h^T \phi_{yy}^{-1} n(t)}{h^T \phi_{yy}^{-1} h}.$$

Figure 10:
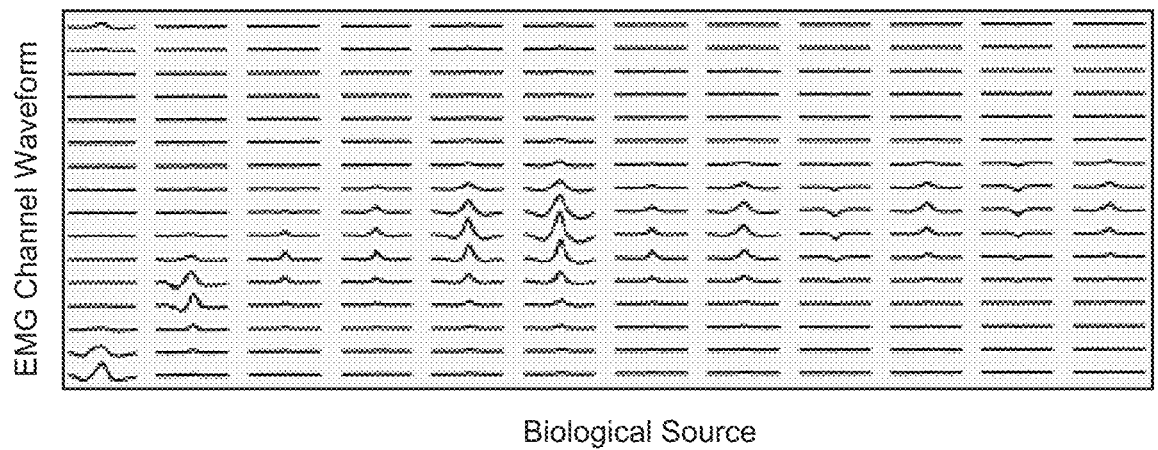
FIG. 10 illustrates a set of EMG channel waveforms associated with a number of biological sources, that may be produced in accordance with some embodiments of the technology described herein.

FIG. 10 illustrates a set of EMG channel waveforms associated with a number of biological sources, that may be produced in accordance with some embodiments of the technology described herein. As shown, each column reflects a spatiotemporal waveform as detected from one biological source (i.e., one motor unit) and each row is (average/template) waveform produced from one EMG channel.

Figure 11:
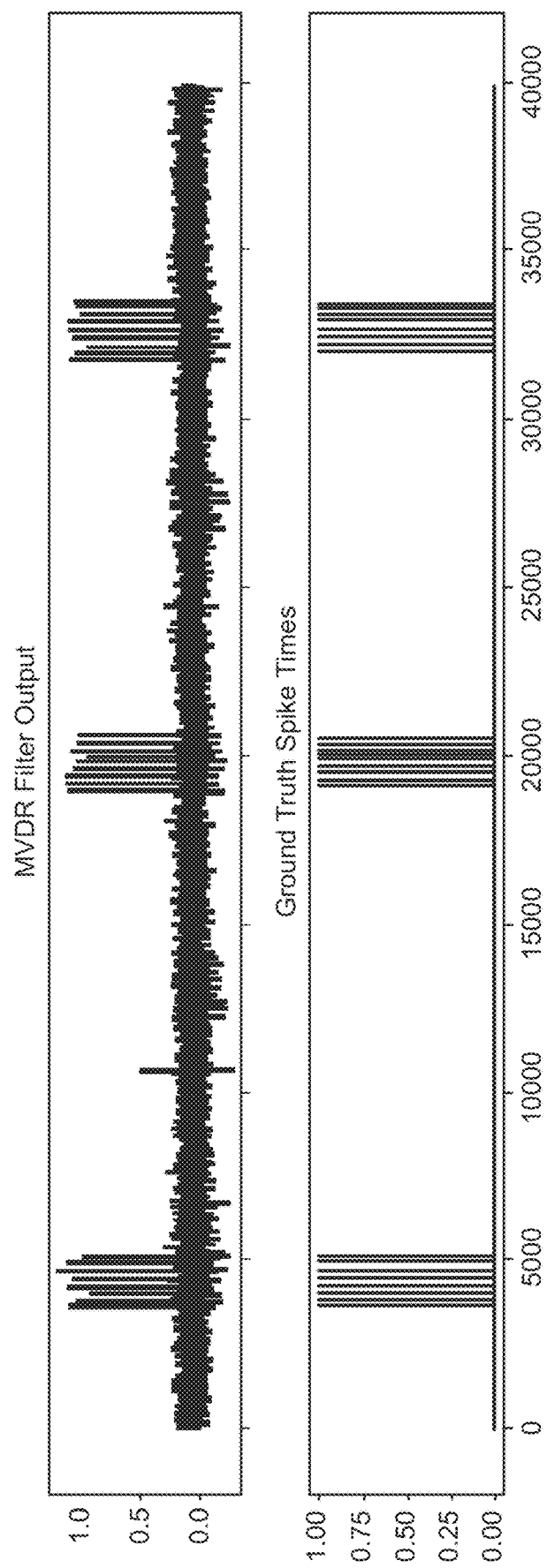
FIG. 11 shows output of an MVDR-based spike event decoder configured in accordance with some embodiments of the technology described herein.
Figure 12:
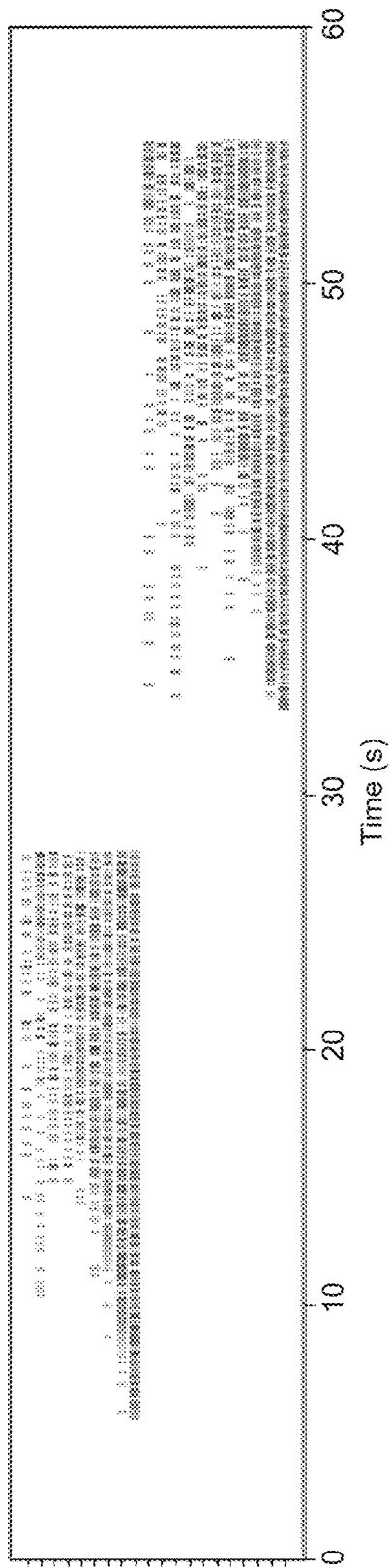
FIG. 12 shows output of an MVDR-based spike event decoder including MVDR filters for each of a plurality of motor units, wherein the decoder is configured in accordance with some embodiments of the technology described herein.

FIG. 11 illustrates an exemplary output of an automatic spike detector using an MVDR filter to process streaming recorded neuromuscular data. As shown, the MVDR filter output is similar to the ground truth spike times indicating that the accuracy of the automatic spike detection is high. When a plurality of MVDR filters are used, each of which corresponds to an individual motor unit, spike event information for each motor unit may be determined, as shown in FIG. 12.

For beamforming techniques such as MVDR, training/fitting the model comprises determining the spatiotemporal response functions. The spatiotemporal patterns for each biological source (e.g., each motor unit) may be determined by first performing spike sorting on an initial set of collected data. To generate the filters, approaches that work in real-time on streaming data and approaches that do not work in real-time (e.g., iterative techniques) may be used. For example, in some embodiments, the spatiotemporal response functions for biological sources are determined using matrix factorization technique. For example, Negro et al. *Journal of Neural Engineering* (2016) uses a multi-step iterative algorithm to decompose the time-lagged sensor signals into components corresponding to each source and detecting the spike events from each source. An advantage of matrix factorization is that it does not require training or parameter fitting, as it acts over the data to effectively accomplish this, e.g., by its iterative nature. More generally, the spatiotemporal response functions can be obtained by any spike decomposition or spike sorting method, of which non-limiting examples include those used by commercially-available spike sorting software packages KiloSort, MountainSort, and combinations of the techniques used therein. In some non-limiting embodiments, estimates of the spatiotemporal response functions are updated, for example by repeating these estimation procedures with additional accumulated data or performing reverse correlation based on the timings of detected spikes during real-time operation of the detectors.

In some embodiments, spike events may be detected in the neuromuscular data. For example, raw neuromuscular data may be thresholded. Alternatively, the recorded neuromuscular data may be whitened or filtered, for example, with wavelets. The detected spike events may then be clustered to identify similar spike events. The spike events in the cluster may then be used to determine the spatiotemporal patterns for each biological source (e.g. by taking the cluster means) for the beamforming filters. Thresholds on the filter outputs may be set by applying the beamforming filters to the data from which the clusters were determined, and determining which threshold results in an appropriate balance between false negatives (failing to identify a member of the cluster) and false positives (e.g. identifying an event from another cluster).

In some embodiments, the clusters are accepted, rejected, or ranked based on quality criteria. Non-limiting examples of quality criteria can reflect intra- and inter-cluster distances, amplitudes of spatiotemporal response functions, biological plausibility of spatiotemporal response functions, and biological plausibility of spike times for events within the cluster (e.g. do multiple events occur within a motor neuron's refractory period). In some embodiments, the event detection and clustering technique described above is repeated multiple times in an iterative manner. For example, after the clusters are identified, the best cluster (e.g., the cluster with the largest amplitude events or the most tightly clustered cluster) is selected and beamforming is used on recorded neuromuscular data to detect spike events corresponding to that cluster, e.g., for a first biological source. The detected spike events are convolved with the spatiotemporal pattern and the result is subtracted from the recorded neuromuscular signals to be used on further iterations for event detection and clustering, essentially eliminating the contribution of the first biological source to the neuromuscular signals. A stopping criterion, e.g., when there are no more clusters that pass a quality criterion or when the residual signal has variance comparable to that of the noise (which can be estimated from a period of minimal neuromuscular activity), may be used to determine when to stop the iteration.

For embodiments that employ neural networks rather than beamforming techniques, there is typically no closed-form solution for the optimal weights in the network. Neural networks that employ supervised learning also require training data with accurate ground-truth labels. Therefore, it can be helpful to generate synthetic training data for training the neural network. Synthetic data may be generated by simulating neuromuscular data having spike times with a random point process (e.g. Poisson process, renewal process), convolving the spike events with spatiotemporal profiles of the spikes. The spatiotemporal profiles can be the cluster centers, samples from within the cluster, interpolations between samples within the clusters, or samples from a model fit from the cluster), and then adding noise. The noise can include Gaussian noise and also spatiotemporal profiles from other motor units (e.g., synthetically generated from a mathematical model, obtained from data from other users, or semisynthetic, e.g., scaled or otherwise transformed profile obtained from another user).

For neural networks, the first convolutional layer of the networks can be initialized with the linear filters determined from beamforming methods, and connections to the output layer may be skipped so that the rest of the network can act as a correction to the beamforming estimates.

In some embodiments, the filters are saved and re-used across user sessions. Due to changes in sensor placement, reusing the filters may require calibration or registration of the signals across sessions.

The inventors have recognized that any of the spike identification systems and methods described herein may optionally comprise a "spike peeling" workflow for iteratively identifying and extracting spikes from distinct biological sources (i.e. motor units). Spike peeling comprises identifying one spike action potential (i.e. one biological source, generally a motor unit) at a time and extracting the spatiotemporal pattern of that biological source from the recording, potentially revealing more spikes in the residual. The purpose of this technique is to be able to extract spikes from a recording in an unsupervised and potentially online manner. In some embodiments, spike peeling may be used to generate a session-specific "spike bank" to extract as many spikes as possible from a recording.

Figure 13:
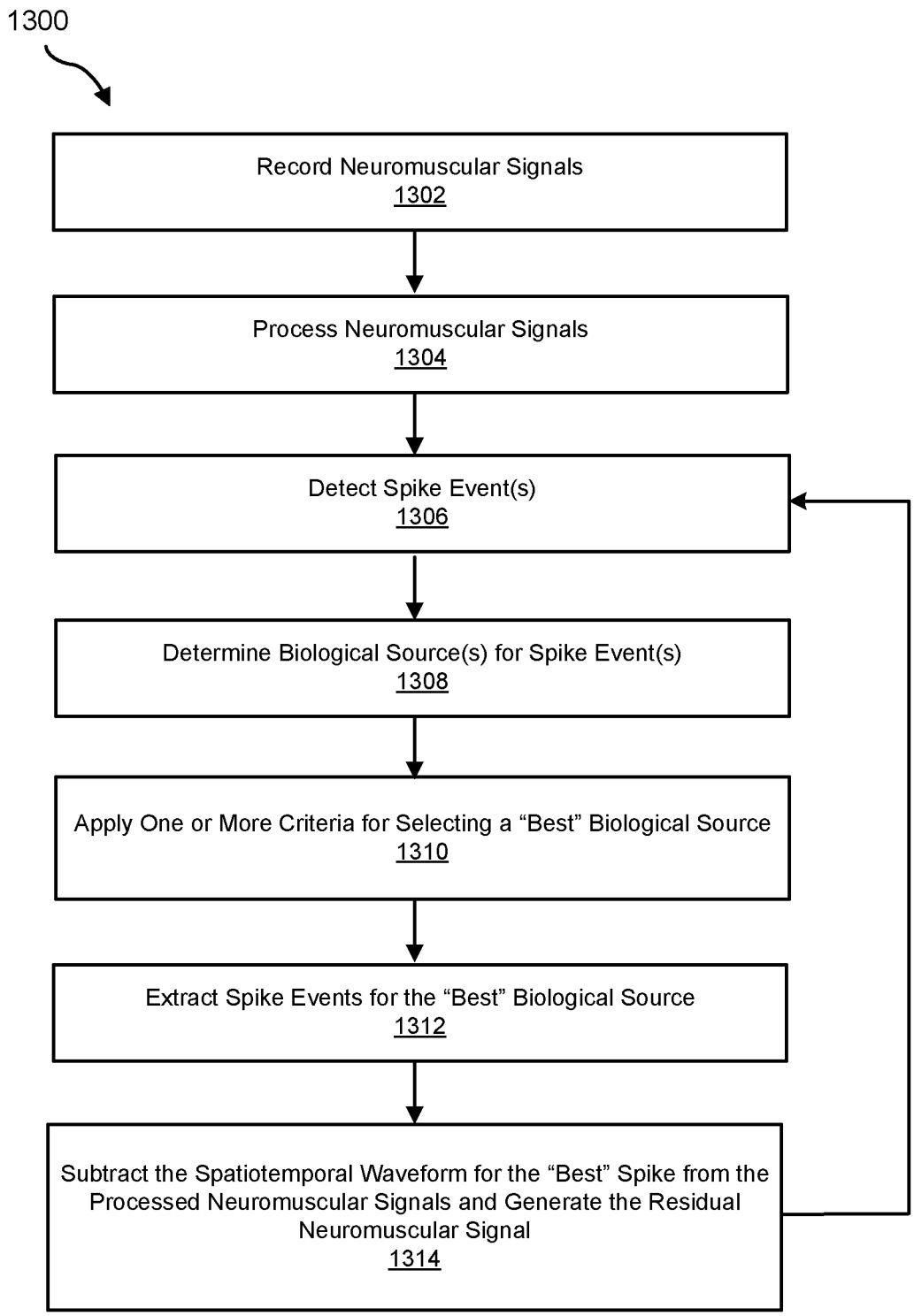
FIG. 13 is a flowchart of a substantially real-time process for detecting spike event information from neuromuscular data in accordance with some embodiments of the technology described herein.

FIG. 13 is a flow chart showing a substantially real-time process for detecting spike event information from neuromuscular data in accordance with some embodiments of the technology described herein. In particular, FIG. 13 shows an example process 1300 for spike peeling according to some embodiments. Such a process may be performed, for example, using various system or computer-based elements as described herein. At block 1302, neuromuscular signals are recorded from a user. Next, the neuromuscular signals are processed at block 1304 and one or more spike events are detected at block 1306 (such as, for example, using beamforming techniques as described herein). At block 1308, the system determines the best biological source(s) for one or more spike event(s) that are detected. A first biological source is selected at block 1310 by applying criteria to determine a "best" biological source (i.e. motor unit) to extract, and the spike events (spike times) are extracted (i.e. saved for use as a control signal or other use) at block 1312. After the spike events for the best biological source are extracted, the spatiotemporal waveform for that biological source (e.g. a spatiotemporal template for that biological source) is subtracted from the processed neuromuscular signals to generate a residual neuromuscular signal at block 1314. Next, spike event(s) are detected from the residual processed neuromuscular signals again and workflow 1306 through 1314 repeats one or more times until no biological source is present in the signal that meets a minimum threshold for selection as a biological source of spike events.

One benefit of spike peeling is that it may be possible to group spikes into "muscles" based on their co-activations and sort spikes within muscles to approximate a recruitment curve.

One effective workflow for spike peeling selects the "best" spike to extract next based on the product of its highest amplitude and the log of the number of spikes assigned to it in the clustering process. The inventors have recognized that using just the highest amplitude as a criterion for selecting the next spike for extraction tends to pick up artifacts that are localized in a single sample in a single electrode, whereas using a criterion based only on the number of detected spikes tends to pick up common low-amplitude patterns that are not spike-like (i.e. not physiologically plausible). The combination of spike amplitude and number of detected spikes is most effective, in at least some instances, to identify spatiotemporal patterns that exhibit physiological characteristics.

Example Wearable System

Figure 14A:
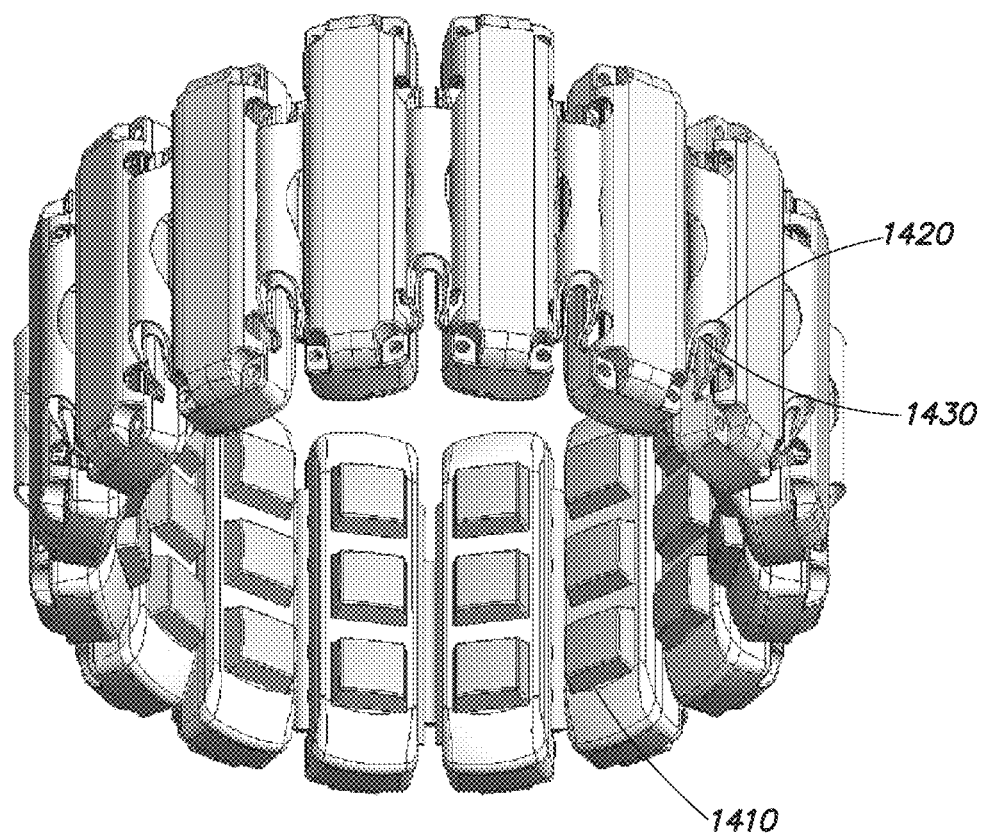
FIG. 14A illustrates a wearable system with sixteen EMG sensors arranged circumferentially around an elastic band configured to be worn around a user's lower arm or wrist, in accordance with some embodiments of the technology described herein.

FIGS. 14A-14B and 15A-15B show several embodiments of a wearable system in which various embodiments may be practiced. In particular, FIG. 14A illustrates a wearable system with sixteen neuromuscular sensors 1410 (e.g., EMG sensors) arranged circumferentially around an elastic band 1420 configured to be worn around a user's lower arm or wrist. As shown, EMG sensors 1410 are arranged circumferentially around elastic band 1420. It should be appreciated that any suitable number of neuromuscular sensors may be used. The number and arrangement of neuromuscular sensors may depend on the particular application for which the wearable device is used. For example, a wearable armband or wristband can be used to generate control information for controlling an augmented reality system, a robot, controlling a vehicle, scrolling through text, controlling a virtual avatar, or any other suitable control task.

Figure 14B:
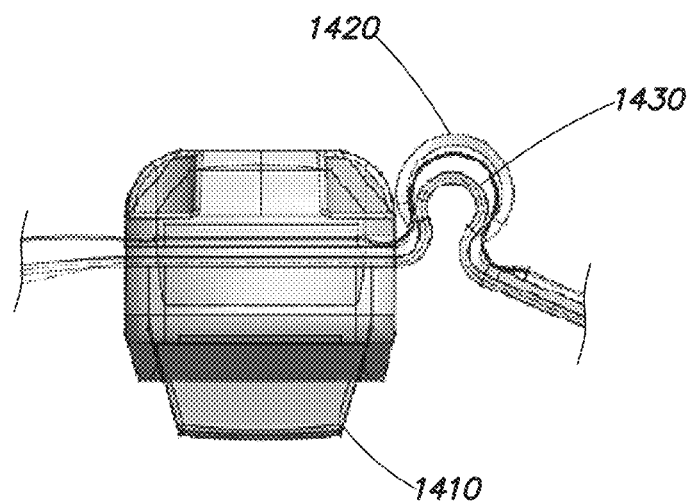
FIG. 14B is a cross-sectional view through one of the sixteen EMG sensors illustrated in FIG. 14.

In some embodiments, sensors 1410 include a set of neuromuscular sensors (e.g., EMG sensors). In other embodiments, sensors 1410 can include a set of neuromuscular sensors and at least one "auxiliary" sensor configured to continuously record auxiliary signals. Examples of auxiliary sensors include, but are not limited to, other sensors such as IMU sensors, microphones, imaging sensors (e.g., a camera), radiation based sensors for use with a radiation-generation device (e.g., a laser-scanning device), or other types of sensors such as a heart-rate monitor. As shown the sensors 1410 may be coupled together using flexible electronics 1430 incorporated into the wearable device. FIG. 14B illustrates a cross-sectional view through one of the sensors 1410 of the wearable device shown in FIG. 14A.

In some embodiments, the output of one or more of the sensing components can be optionally processed using hardware signal processing circuitry (e.g., to perform amplification, filtering, and/or rectification). In other embodiments, at least some signal processing of the output of the sensing components can be performed in software. Thus, signal processing of signals sampled by the sensors can be performed in hardware, software, or by any suitable combination of hardware and software, as aspects of the technology described herein are not limited in this respect. A non-limiting example of a signal processing chain used to process recorded data from sensors 1410 are discussed in more detail below in connection with FIGS. 15A and 15B.

FIGS. 15A and 15B illustrate a schematic diagram with internal components of a wearable system with sixteen EMG sensors, in accordance with some embodiments of the technology described herein. As shown, the wearable system includes a wearable portion 1510 (FIG. 15A) and a dongle portion 1520 (FIG. 15B) in communication with the wearable portion 1510 (e.g., via Bluetooth or another suitable short range wireless communication technology). As shown in FIG. 15A, the wearable portion 1510 includes the sensors 1410, examples of which are described in connection with FIGS. 14A and 14B. The output of the sensors 1410 is provided to analog front end 1530 configured to perform analog processing (e.g., noise reduction, filtering, etc.) on the recorded signals. The processed analog signals are then provided to analog-to-digital converter 1532, which converts the analog signals to digital signals that can be processed by one or more computer processors. An example of a computer processor that may be used in accordance with some embodiments is microcontroller (MCU) 1534 illustrated in FIG. 15A. As shown, MCU 1534 may also include inputs from other sensors (e.g., IMU sensor 1540), and power and battery module 1542. The output of the processing performed by MCU may be provided to antenna 1550 for transmission to dongle portion 1520 shown in FIG. 15B.

Dongle portion 1520 includes antenna 1552 configured to communicate with antenna 1550 included as part of wearable portion 1510. Communication between antenna 1550 and 1552 may occur using any suitable wireless technology and protocol, non-limiting examples of which include radiofrequency signaling and Bluetooth. As shown, the signals received by antenna 1552 of dongle portion 1520 may be provided to a host computer for further processing, display, and/or for effecting control of a particular physical or virtual object or objects.

Although the examples provided with reference to FIGS. 14A, 14B and FIGS. 15A, 15B are discussed in the context of interfaces with EMG sensors, it is understood that the techniques described herein for reducing electromagnetic interference can also be implemented in wearable interfaces with other types of sensors including, but not limited to, mechanomyography (MMG) sensors, sonomyography (SMG) sensors, and electrical impedance tomography (EIT) sensors.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A computerized system, comprising:
a plurality of neuromuscular sensors configured to record a plurality of neuromuscular signals that arise from the central nervous system of a user, wherein the plurality of neuromuscular sensors are arranged on one or more wearable devices; and
at least one computer processor programmed to:
detect, based on the plurality of neuromuscular signals or information derived from the plurality of neuromuscular signals, at least one spike event corresponding to firing of an action potential in at least one motor unit;
determine, based on the plurality of neuromuscular signals or the information derived from the plurality of neuromuscular signals, a biological source of the detected at least one spike event; and generate, in substantially real-time, at least one control signal for operation of at least one device, wherein the at least one control signal is based, at least in part, on the detected at least one spike event; and the at least one computer processor is further programmed to detect the at least one spike event using an iterative process comprising:

subtracting a detected spike event waveform from at least one of the plurality of neuromuscular signals to generate a residual neuromuscular signal;

attempting to detect additional spike events in the residual neuromuscular signal; and stopping the iterative detection process when no additional spike events are detected in the residual neuromuscular signal.

2. The computerized system of claim 1, wherein the at least one computer processor is further programmed to:

apply one or more criteria for selecting a biological source from a plurality of biological sources associated with respective detected spike events; and select at least one spike event associated with the biological source.

3. The computerized system of claim 2, wherein the at least one computer processor is further programmed to perform the iterative process by processing the detected spike events until none of the biological sources are present within the residual signal that meets a minimum threshold for selection as the biological source for spike events.

4. The computerized system of claim 1, wherein the at least one computer processor is further programmed to group the detected spike events, including the detected at least one spike event, into a muscle-specific group based on co-activations and sort spike events within the muscle-specific group to approximate a recruitment curve.

5. The computerized system of claim 1, wherein the at least one computer processor is further programmed to apply at least one filter to a time-lagged representation of the plurality of neuromuscular signals, and wherein the detecting the at least one spike event and the determining the biological source of the detected at least one spike event is performed based on the filtered time-lagged representation of the plurality of neuromuscular signals.

6. The computerized system of claim 5, wherein the applying the at least one filter to the time-lagged representation of the plurality of neuromuscular sensors comprises using a beamforming process to apply a plurality of beamforming filters to the time-lagged representation of the plurality of neuromuscular signals, wherein the plurality of beamforming filters are filters generated based on spatiotemporal patterns of one or more spike events.

7. The computerized system of claim 6, wherein the beamforming process comprises using at least one of a minimum variance distortionless response technique and a linear constrained minimum variance technique.

8. The computerized system of claim 6, wherein the at least one computer processor is further programmed to determine the spatiotemporal patterns of the one or more spike events corresponding to the plurality of beamforming filters.

9. The computerized system of claim 8, wherein the determining the spatiotemporal patterns of the one or more spike events corresponding to the plurality of beamforming filters comprises:

detecting a plurality of spike events in the recorded neuromuscular signals;

clustering the detected plurality of spike events; and determining the spatiotemporal patterns based on the clusters of spike events.

10. The computerized system of claim 8, wherein the detecting a plurality of spike events comprises:

detecting within the plurality of neuromuscular signals, periods of low activity; and detecting within the period of low activity, putative spike events.

11. The computerized system of claim 10, wherein the detecting the plurality of spike events further comprises analyzing the detected putative spike events to discard spike events having one or more particular characteristics, and wherein the one or more particular characteristics include a duration longer than a particular threshold duration.

12. The computerized system of claim 5, wherein the at least one computer processor is further programmed to threshold the filtered time-lagged representation of the plurality of neuromuscular signals to detect the at least one spike event.

13. The computerized system of claim 1, wherein the at least one computer processor is further programmed to detect the at least one spike event and/or determine the biological source of the detected at least one spike event using one or more neural networks, comprising at least one of a convolutional neural network and a recurrent neural network.

14. The computerized system of claim 1, wherein the at least one computer processor is further programmed to detect the at least one spike event and determine the biological source of the detected at least one spike event using a multi-step iterative technique to decompose a time-lagged representation of the plurality of neuromuscular signals into signal components corresponding to at least one biological source, and detecting the at least one spike event from the at least one biological source.

15. The computerized system of claim 1, wherein the generating the at least one control signal comprises generating compressed data including an indication of the at least one spike event, wherein the indication of the at least one spike event is provided as the at least one control signal to the at least one device, wherein the at least one device comprises a computer-based system, and wherein the indication of the at least one spike event is provided as at least one of a group comprising:

a discrete control signal;

a continuous control signal; and a composite control signal.

16. The computerized system of claim 1, wherein the generating the at least one control signal comprises generating an indication of the at least one spike event, and wherein the indication of the at least one spike event includes an indication of the biological source of the at least one spike event and a time of occurrence of the at least one spike event.

17. The computerized system of claim 1, wherein the at least one computer processor is programmed to provide feedback to the user responsive to the at least one control signal based, at least in part, on the detected at least one spike event and/or the determined biological source of the detected at least one spike event.

18. The computerized system of claim 1, further comprising an inertial sensor configured to determine movement artifacts or shifts in spatial location of muscle fibers of the at least one motor unit relative to one or more of the plurality of neuromuscular sensors.

19. The computerized system of claim 1, wherein the detecting the at least one spike event comprises detecting a spatiotemporal pattern of the at least one spike event, and
wherein generating the at least one control signal comprises the generating the at least one control signal based, at least in part, on at least one characteristic of the detected spatiotemporal pattern of the at least one spike event while the plurality of neuromuscular signals are recorded.

20. The computerized system of claim 19, wherein the at least one characteristic comprises a rate of the at least one spike event and/or a spatial distribution of the detected spatiotemporal pattern of the at least one spike event.

21. The computerized system of claim 1, wherein the determined biological source comprises at least one of a group comprising:
a motor unit;
a plurality of motor units;
a muscle; and
a plurality of muscles.

22. The computerized system of claim 1, wherein the determining the biological source of the at least one spike event comprises determining that the at least one spike event is associated with a motor unit or group of motor units,
wherein the at least one computer processor is further programmed to determine a muscle to which the motor unit or group of motor units belongs, and
the generating the at least one control signal comprises generating the at least one control signal based on the determined muscle to which the motor unit or group of motor units belongs.

23. The computerized system of claim 22, wherein the determined muscle is associated with a motor unit recruitment sequence describing a sequence of activation of motor units for the determined muscle, and
wherein the at least one computer processor is further programmed to determine where the motor unit or group of motor units fall within the motor unit recruitment sequence of the determined muscle.

24. The computerized system of claim 1, further comprising:
at least one auxiliary sensor configured to record a plurality of auxiliary signals, and
wherein the at least one computer processor is further programmed to generate the at least one control signal based, at least in part, on the plurality of auxiliary signals.

25. The computerized system of claim 24, wherein the at least one computer processor is programmed to provide feedback to the user as part of a user training process, and wherein the feedback includes at least one of a group comprising auditory, visual, haptic, and multi-sensory feedback.

26. The computerized system of claim 24, wherein the at least one auxiliary sensor comprises at least one inertial measurement unit (IMU) sensor configured to record a plurality of IMU signals, and
wherein the at least one computer processor is further programmed to generate the at least one control signal based, at least in part, on the plurality of IMU signals and/or information derived from the plurality of IMU signals.

27. The computerized system of claim 24, wherein the at least one auxiliary sensor comprises at least one camera configured to record one or more images, and
wherein the at least one computer processor is further programmed to generate the at least one control signal based, at least in part, on the one or more images and/or information derived from the one or more images.

28. The computerized system of claim 1, wherein the at least one computer processor comprises at least one first computer processor included as a portion of an element separate from and in communication with the plurality of neuromuscular sensors arranged on the one or more wearable devices and at least one second computer processor integrated with the one or more wearable devices on which the plurality of neuromuscular sensors are arranged, and wherein the plurality of neuromuscular sensors are configured to transmit at least some of the plurality of neuromuscular signals to the at least one first computer processor,
wherein the at least one first computer processor is programmed to:
train, based on the at least some of the plurality of neuromuscular signals transmitted from the plurality of neuromuscular sensors, at least one spike detection model and/or at least one spike identification model; and
transmit the trained at least one spike detection model and/or the at least one spike identification model to the at least one second computer processor, and
wherein the at least one second computer processor is programmed to detect the at least one spike event and determine the biological source of the detected at least one spike event using the at least one spike detection model and/or the at least one spike identification model transmitted from the at least one first computer processor.

29. The computerized system of claim 28, wherein the at least one spike detection model and/or the least one spike identification model are trained to estimate at least one of a group comprising:
whether the user is activating a particular motor unit;
whether the user is activating a particular motor unit with a particular timing; and
whether the user is activating a particular combination of motor units.

30. The computerized system of claim 1, wherein the detecting the at least one spike event corresponding to the firing of the action potential in the at least one motor unit comprises detecting at least one spike event corresponding to firing of an action potential in a plurality of motor units.

* * * * *

UNITED STATES PATENT AND TRADEMARK OFFICE
CERTIFICATE OF CORRECTION

PATENT NO. : 11,179,066 B2
APPLICATION NO. : 16/539755
DATED : November 23, 2021
INVENTOR(S) : Patrick Kaifosh et al.

Page 1 of 1

It is certified that error appears in the above-identified patent and that said Letters Patent is hereby corrected as shown below:

In the Claims

In Column 33, Lines 7-8, Claim 19, delete "wherein generating the at least one control signal comprises the generating the at least one control signal" and insert -- wherein the generating the at least one control signal comprises generating the at least one control signal --, therefor.

In Column 34, Line 44, Claim 29, delete "the" and insert -- the at --, therefor.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*